(12) United States Patent
Wada et al.

(10) Patent No.: US 9,504,767 B2
(45) Date of Patent: *Nov. 29, 2016

(54) ABSORBENT ARTICLE

(71) Applicant: UNICHARM CORPORATION, Shikokuchuo-shi, Ehime (JP)

(72) Inventors: Ichiro Wada, Kanonji (JP); Masashi Nakashita, Kanonji (JP); Masashi Uda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/430,789

(22) PCT Filed: Aug. 20, 2013

(86) PCT No.: PCT/JP2013/072184
§ 371 (c)(1),
(2) Date: Mar. 24, 2015

(87) PCT Pub. No.: WO2014/050368
PCT Pub. Date: Apr. 3, 2014

(65) Prior Publication Data
US 2015/0250917 A1    Sep. 10, 2015

(30) Foreign Application Priority Data

Sep. 28, 2012    (JP) ................. 2012-218870

(51) Int. Cl.
*A61F 13/15*    (2006.01)
*A61L 15/20*    (2006.01)
(Continued)

(52) U.S. Cl.
CPC ............ *A61L 15/20* (2013.01); *A61F 13/4756* (2013.01); *A61F 13/512* (2013.01);
(Continued)

(58) Field of Classification Search
CPC ............... A61F 13/5113; A61F 13/51104; A61F 13/52; A61F 13/511; A61F 13/513; A61F 2013/51059; A61F 2013/51061
USPC ................ 604/367, 364, 378, 381, 382
See application file for complete search history.

(56) References Cited

U.S. PATENT DOCUMENTS 6,258,196 B1    7/2001    Suzuki et al.
2006/0063457 A1    3/2006    Matsui et al.
(Continued)

FOREIGN PATENT DOCUMENTS

EP    2821041 A1    1/2015
JP    2004-218183 A    8/2004
(Continued)

OTHER PUBLICATIONS

Kikutani, T., et al., "Fiber Structure Formation in High-speed Melt Spinning of Sheath-Core Type Bicomponent Fibers," Journal of the Society of Fiber Science and Technology, vol. 51, No. 9, 1995, pp. 408-415.

(Continued)

*Primary Examiner* — Jacqueline Stephens
(74) *Attorney, Agent, or Firm* — Hauptman Ham, LLP

(57) ABSTRACT

The present invention addresses the problem of providing an absorbent article that has an improved ability to transfer menstrual blood from a liquid-permeable layer to an absorbent body and can reduce the amount of the menstrual blood remaining in the liquid-permeable layer. To solve this problem, provided is a sanitary napkin provided with a top sheet, a back sheet and an absorbent body that is interposed between the top sheet and the back sheet, wherein convex portions formed in an excretion orifice contact region of the top sheet are coated with a blood lubricity-imparting agent that has a kinetic viscosity of 0.01-80 $mm^2/s$ at 40° C., a water retention rate of 0.01-4.0 mass % and a weight-average molecular weight of less than 1,000.

11 Claims, 8 Drawing Sheets

(51) Int. Cl.
*A61F 13/475* (2006.01)
*A61L 15/34* (2006.01)
*A61F 13/84* (2006.01)
*A61L 15/42* (2006.01)
*A61F 13/512* (2006.01)
*A61F 13/51* (2006.01)
*A61F 13/511* (2006.01)
*A61F 13/513* (2006.01)

(52) U.S. Cl.
CPC ... *A61F 13/51104* (2013.01); *A61F 13/51113* (2013.01); *A61F 13/51394* (2013.01); *A61F 13/8405* (2013.01); *A61L 15/34* (2013.01); *A61L 15/42* (2013.01); *A61F 13/511* (2013.01); *A61F 13/513* (2013.01); *A61F 2013/15439* (2013.01); *A61F 2013/51059* (2013.01); *A61F 2013/51061* (2013.01); *A61F 2013/51066* (2013.01); *A61L 2300/20* (2013.01); *A61L 2300/21* (2013.01); *A61L 2300/216* (2013.01); *A61L 2400/10* (2013.01)

(56) References Cited

U.S. PATENT DOCUMENTS

| | | |
|---|---|---|
| 2008/0010795 A1 | 1/2008 | Mizutani et al. |
| 2008/0200894 A1 | 8/2008 | Gatto et al. |
| 2009/0029165 A1 | 1/2009 | Goda |
| 2009/0221978 A1 | 9/2009 | Gatto et al. |
| 2009/0227166 A1 | 9/2009 | Goda |
| 2009/0243141 A1 | 10/2009 | Goda |
| 2012/0164908 A1 | 6/2012 | Kunimoto |
| 2012/0226250 A1* | 9/2012 | Sato ............... A61F 13/51104 604/367 |
| 2014/0052086 A1 | 2/2014 | Komatsu et al. |
| 2015/0032074 A1 | 1/2015 | Nakashita et al. |

FOREIGN PATENT DOCUMENTS

| | | |
|---|---|---|
| JP | 2005-350836 A | 12/2005 |
| JP | 2007-204899 A | 8/2007 |
| JP | 2007-204901 A | 8/2007 |
| JP | 2007-204902 A | 8/2007 |
| JP | 2007-303035 A | 11/2007 |
| JP | 2008-002034 A | 1/2008 |
| JP | 2008-101285 A | 5/2008 |
| JP | 2010-518918 A | 6/2010 |
| JP | 2010-168715 A | 8/2010 |
| JP | 2011-510801 A | 4/2011 |
| JP | 2011-127259 A | 6/2011 |
| JP | 2011-137262 A | 7/2011 |
| JP | 2012-236001 A | 12/2012 |
| WO | 2008/101163 A2 | 8/2008 |
| WO | 2009/102837 A2 | 8/2009 |
| WO | 2013/129236 A1 | 9/2013 |

OTHER PUBLICATIONS

Plastic materials in polymer processing, 1st Edition, Appendix table: "Typical materials used in polymer processing" (ed. Japan Society of Polymer Processing, Sigma Publishing, Feb. 10, 1988).
Fujita, A., "Prediction of Organic Compounds and Organic Conceptual Diagram," Journal of Japanese Chemistry, vol. 11, No. 10, Oct. 1957, pp. 719-725.
International Search Report mailed Nov. 12, 2013 in International Application No. PCT/JP2013/072184, 2 pages.

* cited by examiner

200μm (a)

50 μm (b)

50 μm

ABSORBENT ARTICLE

RELATED APPLICATIONS

The present application is a National Phase of International Application Number PCT/JP2013/072184 filed Aug. 20, 2013 and claims priority of Japanese Application Number 2012-218870 filed Sep. 28, 2012.

TECHNICAL FIELD

The present invention relates to an absorbent article.

BACKGROUND ART

In an absorbent article, such as a sanitary napkin or panty liner, liquid excreta, such as menstrual blood penetrates the liquid-permeable layer, such as the top sheet, and is absorbed and retained by the absorbent body, but due to the high viscosity of menstrual blood it tends to remain in the liquid-permeable layer. When menstrual blood remains in the liquid-permeable layer of an absorbent article, it produces a feeling of stickiness and visual discomfort for the wearer, and it has therefore been a goal to improve the migration of menstrual blood from the liquid-permeable layer to the absorbent body and reduce residual menstrual blood in the liquid-permeable layer.

On the other hand, absorbent articles coated with a lotion composition on the top sheet are known in the prior art (PTLs 1 and 2). In PTL 1, a polypropylene glycol material-containing lotion composition is coated onto the inner surface of a top sheet (the clothing side surface), the inner surface of the back sheet (the body side surface), and on the base material between the inner surface of the top sheet and the inner surface of the back sheet, while in PTL 2, a polypropylene glycol material-containing lotion composition is coated onto the outer surface of a top sheet (the body side surface).

Top sheets having an irregular structure on the surface are also known in the prior art (PTLs 3 and 4). In PTLs 3 and 4, an irregular structure is formed on the surface of a top sheet by heat treatment of a heat-extendable fiber layer that is partially contact bonded or adhesively bonded by contact bonded adhesive sections, and heat stretching of the heat-extendable fiber layer, thereby causing the heat-extendable fiber layer to bulge out to the skin contact surface.

CITATION LIST

Patent Literature

PTL 1 Japanese Unexamined Patent Publication No. 2010-518918
PTL 2 Japanese Unexamined Patent Publication No. 2011-510801
PTL 3 Japanese Unexamined Patent Publication No. 2005-350836
PTL 4 Japanese Unexamined Patent Publication No. 2010-168715

SUMMARY OF INVENTION

Technical Problem

In PTLs 1 to 4, however, the design is not, such as to improve migration of menstrual blood from the liquid-permeable layer, such as the top sheet, to the absorbent body, and reduce residue of menstrual blood in the liquid-permeable layer.

It is therefore an object of the present invention to provide an absorbent article having improved migration of menstrual blood from the liquid-permeable layer to the absorbent body, and reduced residue of menstrual blood in the liquid-permeable layer.

Solution to Problem

In order to solve the problems described above, the invention provides an absorbent article comprising a liquid-permeable layer, a liquid-impermeable layer and an absorbent body situated between the liquid-permeable layer and the liquid-impermeable layer, in which the liquid-permeable layer has a first layer with a skin contact surface and a non-skin contact surface, the first layer being a layer formed by heat stretching of a heat-extendable fiber layer that has been partially compressed by compressed sections, wherein a projection bulges out on the skin contact surface by heat stretching of the heat-extendable fiber layer at least in the excretory opening contact region of the skin contact surface, and at least the projection of the excretory opening contact region are coated with a blood slipping agent having a 40° C. kinematic viscosity of 0.01 to 80 $mm^2/s$, a water holding percentage of 0.01 to 4.0 mass % and a weight-average molecular weight of less than 1,000.

In the absorbent article of the invention, menstrual blood excreted by the wearer and reaching the excretory opening contact region slips down together with the blood slipping agent present in the projections, and migrates through the liquid-permeable layer into the absorbent body. The absorbent article of the invention therefore has improved migration of menstrual blood from the liquid-permeable layer to the absorbent body, and reduced residue of menstrual blood in the liquid-permeable layer. This prevents the skin contact surface of the liquid-permeable layer from having a sticky feel, and maintains a smooth feel. This function and effect of the blood slipping agent is exhibited regardless of changes in menstrual blood discharge during menstruation (that is, whether the amount of discharged menstrual blood is large or small).

Advantageous Effects of Invention

According to the invention there is provided an absorbent article that can improve migration of menstrual blood from the liquid-permeable layer to the absorbent body, and reduce residue of menstrual blood in the liquid-permeable layer.

DESCRIPTION OF EMBODIMENTS

Figure 1:
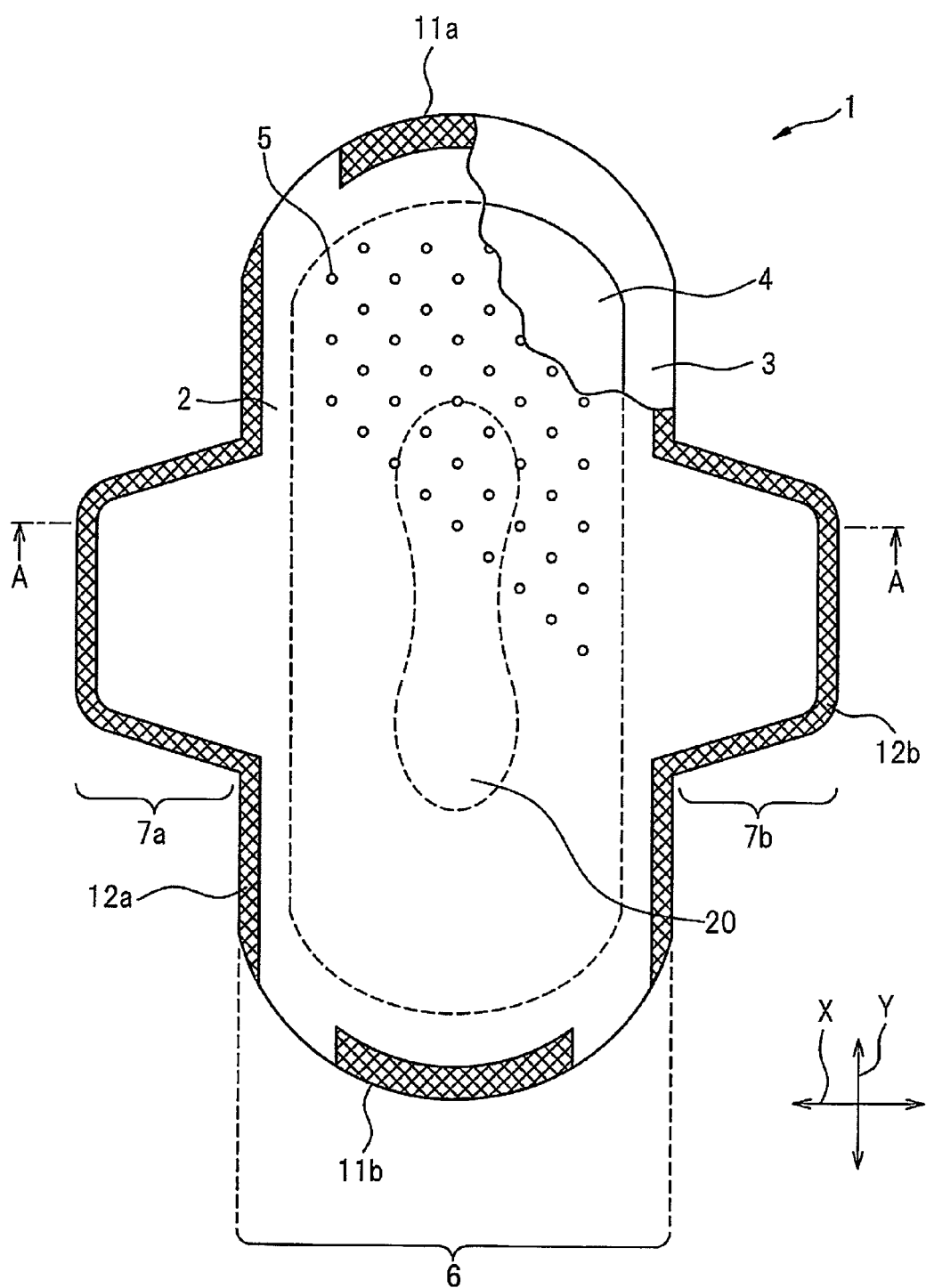
FIG. 1 is a partial cutaway plan view of a sanitary napkin according to one embodiment of the absorbent article of the invention.

The absorbent article of the invention will now be described.

The absorbent article according to aspect 1 is an absorbent article comprising a liquid-permeable layer, a liquid-impermeable layer and an absorbent body situated between the liquid-permeable layer and the liquid-impermeable layer, wherein the liquid-permeable layer has a first layer with a skin contact surface and a non-skin contact surface, the first layer is a layer formed by heat stretching of a heat-extendable fiber layer that has been partially compressed by compressed sections, wherein a projection bulges out on the skin contact surface by heat stretching of the heat-extendable fiber layer at least in the excretory opening contact region of the skin contact surface, and at least the projection of the excretory opening contact region are coated with a blood slipping agent having a 40° C. kinematic viscosity of 0.01 to 80 mm$^2$/s, a water holding percentage of 0.01 to 4.0 mass % and a weight-average molecular weight of less than 1,000.

For the purpose of the absorbent article of the invention, the term "heat-extendable fibers" includes the concept not only of fibers whose actual fiber lengths extend by heat treatment, but also of fibers whose actual fiber lengths do not extend but whose apparent fiber lengths extend by heat treatment (for example, crimped fibers whose apparent fiber lengths are extended when the developed crimping is released).

In a preferred aspect (aspect 2) of the absorbent article according to aspect 1, the liquid-permeable layer has a second layer on the non-skin contact surface side of the first layer.

In a preferred aspect (aspect 3) of the absorbent article of aspect 2, the density of the second layer is higher than the density of the first layer. Migration of menstrual blood from the first layer to the second layer is improved by aspect 3.

In a preferred aspect (aspect 4) of the absorbent article of aspect 3, the density of the second layer is 0.1 g/cm$^3$ or less. According to aspect 4, the function and effect of the blood slipping agent are effectively exhibited without being inhibited by the second layer.

In a preferred aspect (aspect 5) of the absorbent article of aspect 3 or 4, the density of the first layer is 0.05 g/cm$^3$ or less. According to aspect 5, the function and effect of the blood slipping agent are effectively exhibited without being inhibited by the first layer.

In a preferred aspect (aspect 6) of the absorbent article according to any of aspects 1 to 5, the IOB of the blood slipping agent is 0.00 to 0.60.

In an aspect (aspect 7) of the absorbent article according to any of aspects 1 to 6, the blood slipping agent is selected from the group consisting of the following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety;

with the proviso that when 2 or more oxy groups are inserted in the compound of (ii) or (iii), the oxy groups are not adjacent.

In a preferred aspect (aspect 8) of the absorbent article of any of aspects 1 to 7, the blood slipping agent is selected from the group consisting of the following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;

with the proviso that when 2 or more same or different bonds are inserted in the compound of (ii') or (iii'), the bonds are not adjacent.

In a preferred aspect (aspect 9) of the absorbent article according to any of aspects 1 to 8, the blood slipping agent is selected from the group consisting of the following items (A)-(F), and any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

In a preferred aspect (aspect 10) of the absorbent article according to any of aspects 1 to 9, the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, and any combination thereof.

In a preferred aspect (aspect 11) of the absorbent article of any of aspects 1 to 10, the blood slipping agent has a vapor pressure of 0.00 to 0.01 Pa at 1 atmosphere, 40° C.

Two or more of aspects of the absorbent article of the invention may also be combined.

There are no particular restrictions on the type and usage of the absorbent article of the invention. For example, absorbent articles include sanitary products and sanitary articles, such as sanitary napkins and panty liners, which may be for humans or animals other than humans, such as pets. The liquid to be absorbed by the absorbent article is not particularly restricted, but will mainly be liquid excreta, such as menstrual blood.

Embodiments of the absorbent article of the invention will now be described, using a sanitary napkin as an example, with reference to the accompanying drawings.

Figure 2:
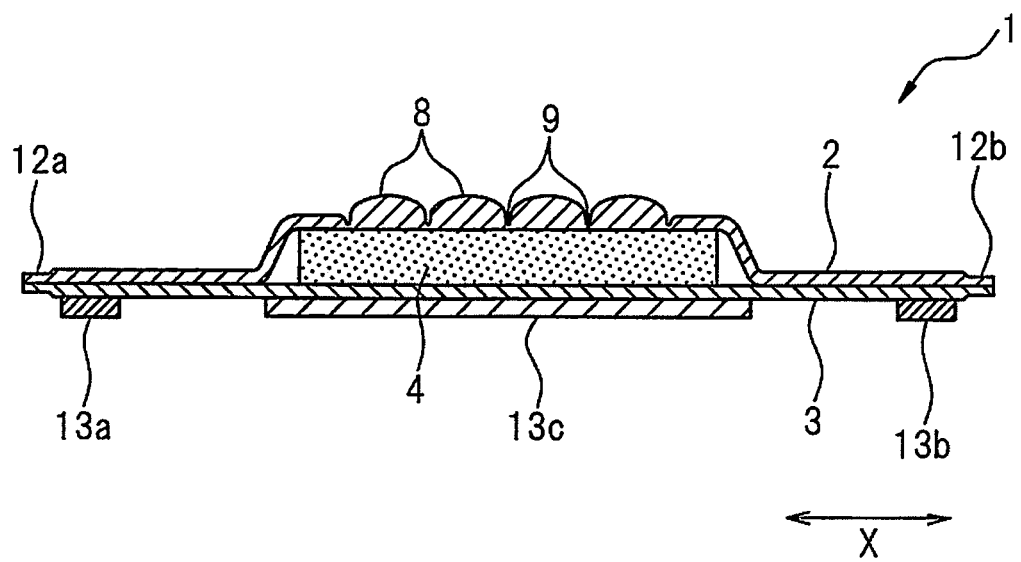
FIG. 2 is a cross-sectional view of FIG. 1 along line A-A.

As shown in FIG. 1 and FIG. 2, the sanitary napkin 1 according to one embodiment of the absorbent article of the invention comprises a liquid-permeable top sheet 2, a liquid-impermeable back sheet 3, and an absorbent body 4 formed between the top sheet 2 and the back sheet 3.

In FIG. 1, the X-axial direction is the widthwise direction of the sanitary napkin 1, the Y-axial direction is the lengthwise direction of the sanitary napkin 1, and the direction of the plane extending in the X-axial and Y-axial directions corresponds to the planar direction of the sanitary napkin 1. The same applies to the other drawings as well.

The sanitary napkin 1 is worn to absorb liquid excreta, such as menstrual blood. It is worn in such a manner that the top sheet 2 is on the skin side of the wearer, and the back sheet 3 is located on the side of the clothing (underwear) of the wearer. Liquid excreta, such as menstrual blood permeates the top sheet 2 and reaches the absorbent body 4, and is absorbed and retained in the absorbent body 4. Leakage of liquid excreta that has been absorbed and retained in the absorbent body 4 is prevented by the back sheet 3.

As shown in FIG. 1, the top sheet 2 and back sheet 3 have their edges bonded together in the lengthwise direction by seal sections 11a, 11b, forming the body section 6, while having their edges bonded together in the widthwise direction by seal sections 12a, 12b, forming essentially rectangular wing sections 7a, 7b that extend out in the widthwise direction from the body section 6.

The shape of the body section 6 can be appropriately adjusted in a range suited to the body of the wearer and to underwear, examples of shapes for the body section 6 including essentially rectangular, essentially elliptical and essentially gourd-like shapes. The dimensions in the lengthwise direction of the body section 6 will usually be 100 to 500 mm and preferably 150 to 350 mm, while the dimensions in the widthwise direction of the body section 6 will usually be 30 to 200 mm and preferably 40 to 180 mm.

The bonding method for the seal sections 11a, 11b, 12a, 12b may be embossing, ultrasonic waves or a hot-melt adhesive. In order to increase the bonding strength, two or more different bonding methods may be combined (for example, bonding with a hot-melt adhesive followed by embossing).

As an example of embossing, the top sheet 2 and back sheet 3 may be passed together between a patterned embossing roll, with patterned projections, and a flat roll, for embossing (a method known as round sealing). By heating the embossing roll and/or flat roll by this method, each sheet is softened so that the seal sections become more distinct. Examples of emboss patterns include lattice-like patterns, zigzag patterns and wavy patterns.

Examples of hot-melt adhesives include pressure-sensitive adhesives and heat-sensitive adhesives composed mainly of rubber-based compounds, such as styrene-ethylene-butadiene-styrene (SEBS), styrene-butadiene-styrene (SBS) or styrene-isoprene-styrene (SIS), or composed mainly of olefin-based compounds, such as linear low-density polyethylene; and water-sensitive adhesives comprising water-soluble polymers (such as polyvinyl alcohol, carboxylmethyl cellulose and gelatin) or water-swelling polymers (such as polyvinyl acetate and sodium polyacrylate). Examples of adhesive coating methods include spiral coating application, coater application, curtain coater application and summit-gun coating.

As shown in FIG. 2, pressure-sensitive adhesive sections 13a, 13b are provided on the clothing side of the back sheet 3 forming the wing sections 7a, 7b, and a pressure-sensitive adhesive section 13c is provided on the clothing side of the back sheet 3 forming the body section 6. The pressure-sensitive adhesive section 13c is attached to the crotch section of underwear, while the wing sections 7a, 7b are folded toward the outer wall of the underwear and the pressure-sensitive adhesive sections 13a, 13b are attached to the crotch section of the underwear, thereby stably anchoring the sanitary napkin 1 to the underwear.

Examples of pressure-sensitive adhesives to be used in the pressure-sensitive adhesive sections 13a, 13b, 13c include styrene-based polymers, such as styrene-ethylene-butylene-styrene block copolymer, styrene-butylene polymer, styrene-butylene-styrene block copolymer and styrene-isobutylene-styrene copolymer; tackifiers, such as C5 petroleum resins, C9 petroleum resins, dicyclopentadiene-based petroleum resins, rosin-based petroleum resins, polyterpene resins and terpenephenol resins; monomer plasticizers, such as tricresyl phosphate, dibutyl phthalate and dioctyl phthalate; and polymer plasticizers, such as vinyl polymer and polyester.

Figure 3:
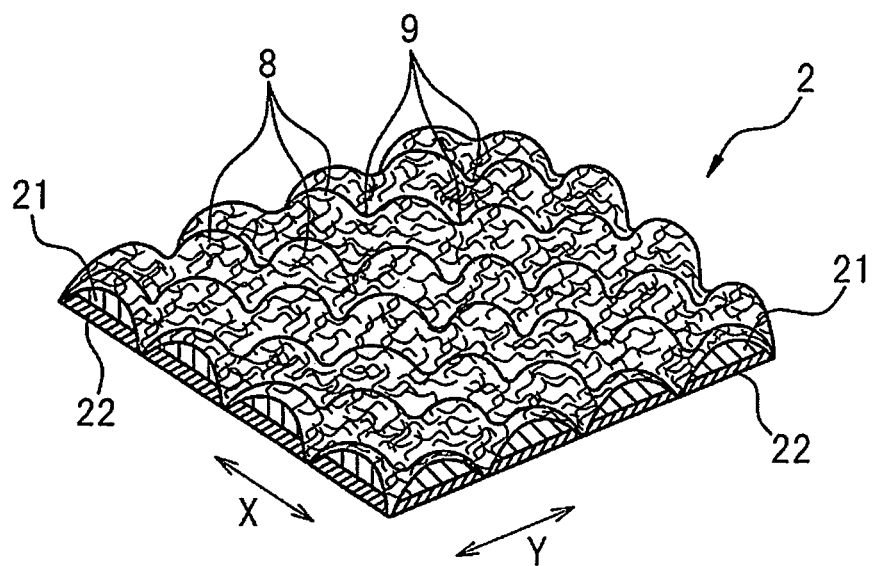
FIG. 3 is a partial perspective view of the top sheet of the sanitary napkin shown in FIG. 1.

The top sheet 2 is a sheet that allows permeation of liquid excreta, such as menstrual blood, an example thereof being a liquid-permeable layer. As shown in FIG. 2 and FIG. 3, a plurality of projections 8 and recesses 9 are formed on the skin contact surface of the top sheet 2 (the top side in FIG. 2 and FIG. 3). Also, as shown in FIG. 3, the top sheet 2 has a first layer 21 and a second layer 22, but the top sheet 2 is shown in a more simplified manner in FIG. 2, omitting the first layer 21 and the second layer 22.

For this embodiment, projections 8 are formed over essentially the entire absorbent body placement region that includes the excretory opening contact region 20 on the skin contact surface of the top sheet 2, it being sufficient for the projections 8 to be formed in at least the excretory opening contact region 20 on the skin contact surface of the top sheet 2. The absorbent body placement region is the region in which the absorbent body 4 overlaps the top sheet 2 when the absorbent body 4 has been projected onto the top sheet 2.

The excretory opening contact region 20 is the region in which the excretory opening of the wearer (for example, the labia minora, labia majora, etc.) contact when the sanitary napkin 1 is worn. The excretory opening contact region 20 is the region delineated by the dotted line in FIG. 1, and it is set at essentially the center of the absorbent body placement region. The location and area of the excretory opening contact region 20 may be adjusted as appropriate. The excretory opening contact region 20 may be set to be essentially the same region as the region that actually contacts with the excretory opening, or it may be set as a larger region, but from the viewpoint of preventing leakage of liquid excreta, such as menstrual blood to the exterior, it is preferably set as a region larger than the region that actually contacts with the excretory opening. The length of the excretory opening contact region 20 will usually be 50 to 200 mm and is preferably 70 to 150 mm, and the width will usually be 10 to 80 mm and is preferably 20 to 50 mm.

For this embodiment, the excretory opening contact region 20 is set as a virtual region, but it may instead be set as a visually recognizable region. Visual recognition may be produced by coloration of the excretory opening contact region 20, or by formation of recesses around the excretory opening contact region 20 (for example, recesses formed by heat embossing treatment).

While not shown here, essentially the entire excretory opening contact region 20 is coated with a blood slipping agent having a 40° C. kinematic viscosity of 0.01 to 80 mm²/s, a water holding percentage of 0.01 to 4.0 mass % and a weight-average molecular weight of less than 1,000. The details regarding the blood slipping agent will be described in a different section.

For this embodiment, essentially the entire excretory opening contact region 20 is coated with the blood slipping agent, but it is sufficient to coat the blood slipping agent on at least the projections 8 of the excretory opening contact region 20. So long as the blood slipping agent is coated on at least the projections 8 of the excretory opening contact region 20, it may also be coated on sections other than the projections 8 of the excretory opening contact region 20 (for example, the recesses 9), or it may be coated in regions other than the excretory opening contact region 20 on the skin contact surface (for example, the regions surrounding the excretory opening contact region 20). For example, the blood slipping agent may be coated essentially over the entire skin contact surface or essentially over the entire absorbent body placement region.

If the blood slipping agent is coated on at least the projections 8 of the excretory opening contact region 20, the following function and effect will be exhibited. When menstrual blood excreted by the wearer reaches the excretory opening contact region 20, it slips together with the blood slipping agent present in the projections 8 down into the recesses 9, and migrates through the top sheet 2 into the absorbent body 4. Therefore, the sanitary napkin 1 has improved migration of menstrual blood from the top sheet 2 to the absorbent body 4, and can reduce residue of menstrual blood in the top sheet 2. This prevents the skin contact surface of the top sheet 2 from having a sticky feel, and maintains a smooth feel. This function and effect of the blood slipping agent is exhibited regardless of changes in menstrual blood discharge during menstruation (that is, whether the amount of discharged menstrual blood is large or small).

Since this embodiment has projections 8 and recesses 9 in the excretory opening contact region 20 such that the excretory opening contact region 20 has an irregular structure, the function and effect of the blood slipping agent is effectively exhibited. The function and effect of the blood slipping agent can be reinforced by coating the blood slipping agent on the recesses 9 in addition to the projections 8.

Incidentally, since the blood slipping agent functions as a lubricating agent to reduce friction between fibers, it can improve the flexibility of the top sheet 2 as a whole.

The sanitary napkin 1 does not require components, such as emollients and immobilizing agents, unlike in known absorbent articles containing skin care compositions, lotion compositions and the like, and the blood slipping agent alone may be applied to the top sheet 2.

The basis weight of the blood slipping agent may usually be about 1 to 30 g/m², preferably about 2 to 20 g/m² and even more preferably about 3 to 10 g/m². If the basis weight of the blood slipping agent is lower than about 1 g/m², menstrual blood will tend to remain in the top sheet 2, while if the basis weight of the blood slipping agent is greater than about 30 g/m², there will tend to be an increase in the sticky feel during wear.

The basis weight of the blood slipping agent can be measured in the following manner, for example.

(1) The region of the top sheet that is to be measured is cut out using a sharp blade, such as a cutter replacement blade, while minimizing any alteration in thickness, to obtain a sample.

(2) The area of the sample: SA (m²) and the mass: $SM_0$ (g) are measured.

(3) The sample is stirred for at least 3 minutes in a solvent that can dissolve the blood slipping agent, such as ethanol or acetone, to dissolve the blood slipping agent in the solvent.

(4) The sample is filtered on mass-measured filter paper, and the sample is thoroughly rinsed with the solvent on the filter paper. The sample on the filter paper is dried in an oven at 60° C.

(5) The masses of the filter paper and sample are measured, and the mass of the filter paper is subtracted to calculate the dry sample mass: $SM_1$ (g).

(6) The basis weight BBS (g/m²) of the blood slipping agent is calculated by the following formula.

$$BBS\ (g/m^2) = [SM_0\ (g) - SM_1\ (g)]/SA\ (m^2)$$

In order to minimize error, multiple samples are taken from multiple absorbent articles, without the total area of the sample exceeding 100 cm², conducting several repeated measurements and taking the average value.

The blood slipping agent is preferably coated without obstructing the voids between the fibers of the top sheet 2. For example, the blood slipping agent may be adhering as droplets or particulates on the surfaces of the fibers of the top sheet 2, or covering the surfaces of the fibers.

The blood slipping agent is preferably coated so that the surface area is increased. This will increase the contact area between the blood slipping agent and the menstrual blood and facilitate slipping of the blood slipping agent together with the menstrual blood. When the blood slipping agent is present as droplets or particulates, the particle diameters can be reduced to increase the surface area.

Examples of methods for coating the blood slipping agent include methods that employ coating applicators (for example, non-contact coaters, such as spiral coaters, curtain coaters, spray coaters and dip coaters. and contact coaters). Non-contact coaters are preferred coating applicators. This will allow the droplet or particulate blood slipping agent to evenly disperse over the entirety, while reducing damage to the top sheet 2.

The blood slipping agent may, if desired, be applied as a coating solution containing a volatile solvent, such as an alcohol-based solvent, ester-based solvent or aromatic solvent. If the coating solution includes a volatile solvent, the viscosity of the coating solution containing the blood slipping agent will be lowered, thereby allowing the application steps to be simplified, facilitating application and making heating during application unnecessary.

The blood slipping agent may be coated directly, if it is a liquid at room temperature, or it may be heated to lower the viscosity, and when it is a solid at room temperature, it may be heated to liquefaction and coated with a control seam HMA (Hot Melt Adhesive) gun. By increasing the air pressure of the control seam HMA gun, it is possible to coat the blood slipping agent as fine particulates. The coating amount of the blood slipping agent can be adjusted, for example, by adjusting the discharged amount from a control seam HMA gun.

The blood slipping agent may be coated during production of the top sheet 2, or it may be coated in the manufacturing line for the sanitary napkin 1. From the viewpoint of minimizing equipment investment, the blood slipping agent is preferably coated in the manufacturing line for the sanitary napkin 1, and in order to prevent shedding of the blood slipping agent which may contaminate the line, the blood slipping agent or its composition is preferably coated during a step downstream from the manufacturing line, and specifically, immediately before encapsulation of the product in an individual package.

Figure 4:
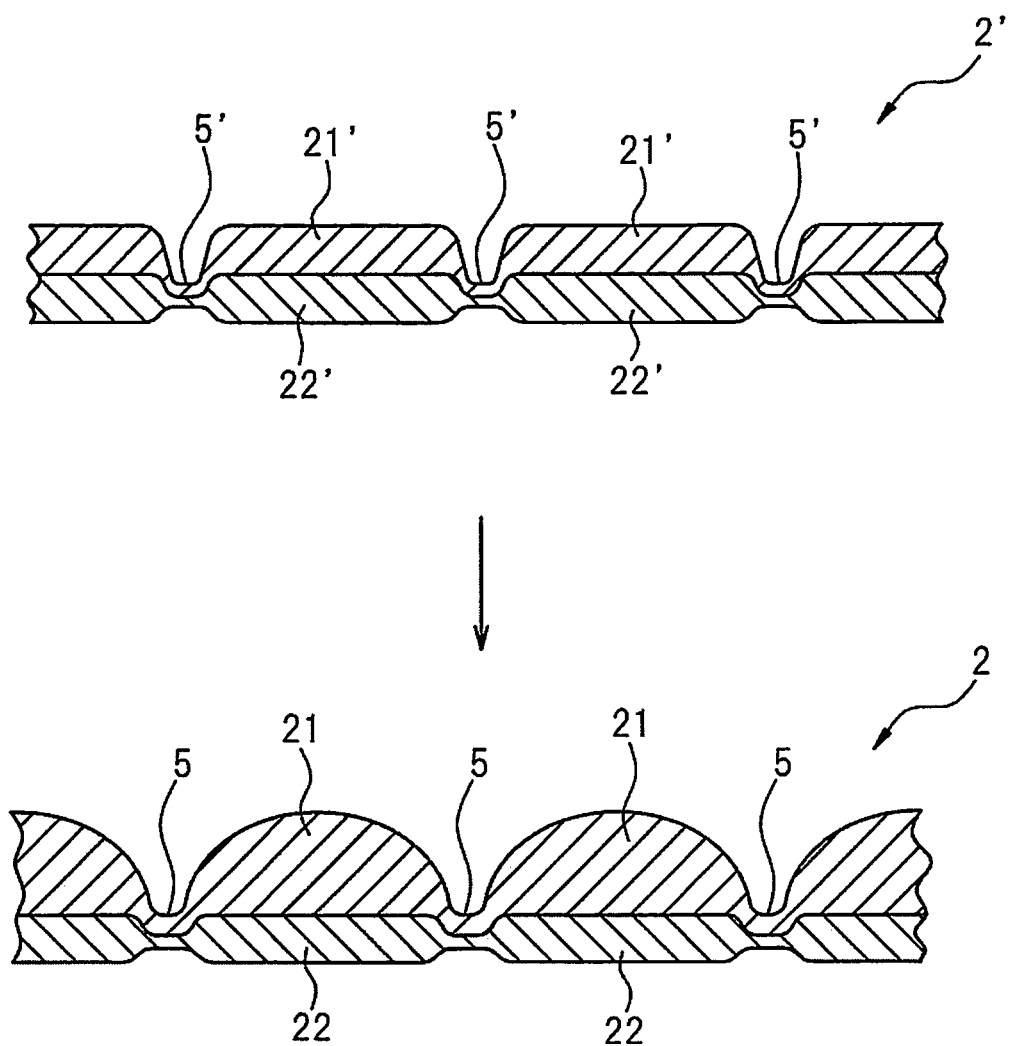
FIG. 4 is a partial magnified cross-sectional view showing the process by which a top sheet is produced by heat stretching treatment.

As shown in FIG. 3 and FIG. 4, the top sheet 2 has a first layer 21 having a skin contact surface and a non-skin contact surface, and a second layer 22 provided on the non-skin contact surface side of the first layer 21.

One side of the first layer 21 (the top side in FIG. 3 and FIG. 4) is the skin contact surface, and the other side (the bottom side in FIG. 3 and FIG. 4) is the non-skin contact surface. As shown in FIG. 3 and FIG. 4, a second layer 22 is layered on the non-skin contact surface of the first layer 21, so that the top sheet 2 has a two-layer structure. The top sheet 2 may also have one or more third layers in addition to the first layer 21 and the second layer 22. So long as the second layer 22 is provided on the non-skin contact surface side of the first layer 21, there are no particular restrictions on the location where the third layer is provided. For example, one or more third layers may be provided between the first layer 21 and the second layer 22. Alternatively, one or more third layers may be provided on the side of the second layer 22 opposite the first layer 21 side. The third layer may be a non-heat-extendable fiber layer or a heat-extendable fiber layer. Furthermore, so long as it does not interfere with the deformation that occurs with heat stretching of the heat-extendable fiber layer 21' (especially bulging to the skin contact surface side), the third layer may have another layer in addition to the fiber layer (for example, an adhesive layer).

As shown in FIG. 4, the top sheet 2 is produced by heat stretching treatment of a laminated sheet 2' having a heat-extendable fiber layer 21', a non-heat-extendable fiber layer 22', and compressed sections 5' that partially bond the heat-extendable fiber layer 21' and non-heat-extendable fiber layer 22', wherein the heat treated heat-extendable fiber layer 21' and non-heat-extendable fiber layer 22' after heat stretching treatment correspond to the first layer 21 and the second layer 22, respectively.

Figure 6:
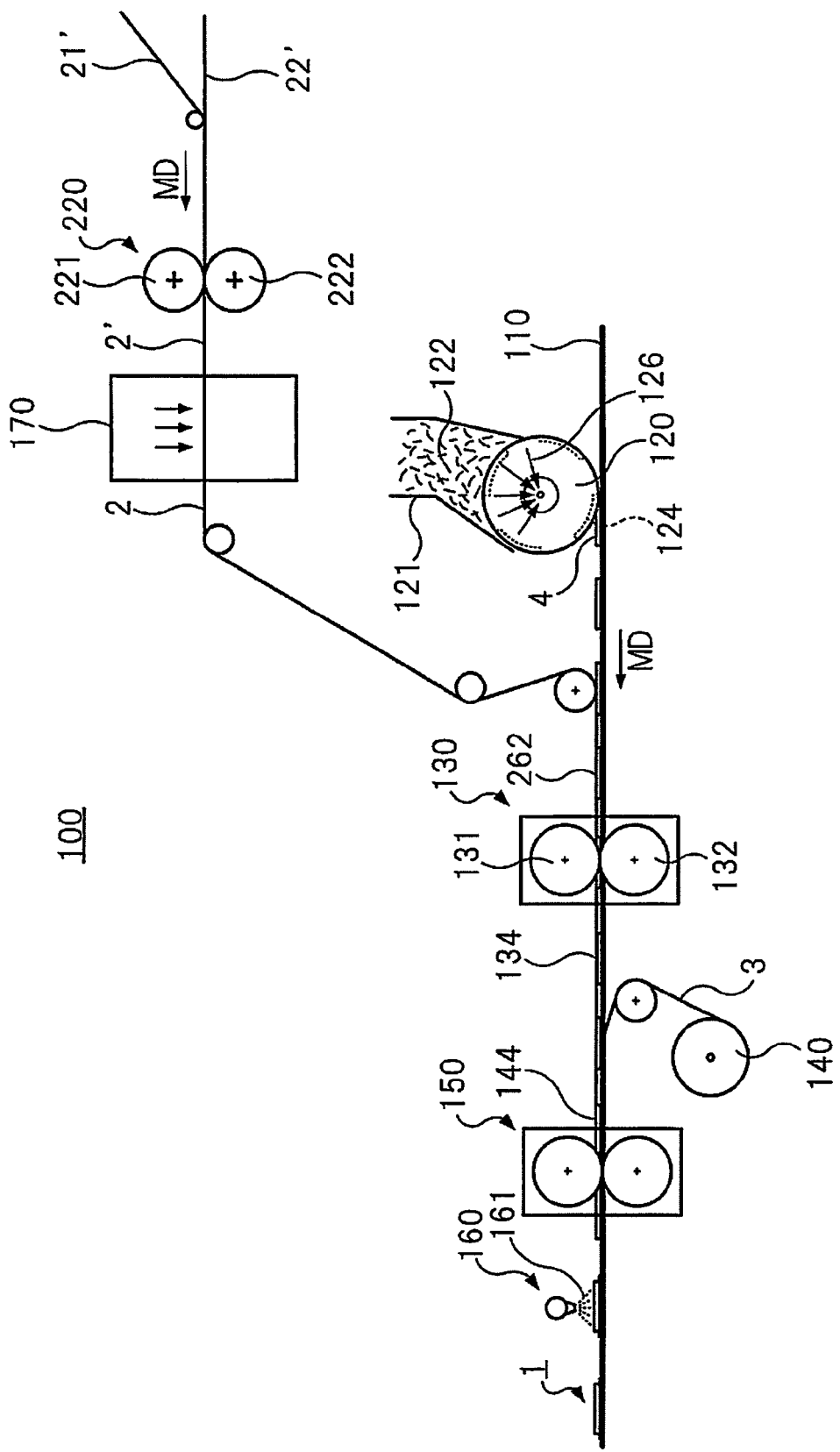
FIG. 6 is a diagram illustrating a method for producing a sanitary napkin.

As shown in FIG. 6, the laminated sheet 2' can be produced by laminating the heat-extendable fiber layer 21' and the non-heat-extendable fiber layer 22', produced by prescribed methods, as the upper layer and lower layer, respectively, and then passing them between the upper roll 221 and lower roll 222 of an embossing apparatus 220.

The heat-extendable fiber layer 21' is a layer containing one or more different heat-extendable fibers.

The heat-extendable fibers may be fibers whose actual fiber lengths extend by heat treatment (for example, fibers wherein the resin crystal state is altered so that the actual fiber lengths extend), or fibers whose actual fiber lengths do not extend but whose apparent fiber lengths extend by heat treatment (for example, crimped fibers wherein developed zigzag, Ω-shaped or spiral-shaped crimping is released such that the apparent fiber lengths extend).

Various heat-extendable fibers are known (for example, Japanese Unexamined Patent Publication No. 2004-218183, Japanese Unexamined Patent Publication No. 2005-350836, Japanese Unexamined Patent Publication No. 2007-303035, Japanese Unexamined Patent Publication No. 2007-204899, Japanese Unexamined Patent Publication No. 2007-204901, Japanese Unexamined Patent Publication No. 2007-204902 and Japanese Unexamined Patent Publication No. 2008-101285), and may be selected as appropriate.

Examples of heat-extendable fibers include two-component heat-extendable composite fibers comprising two different resins with different melting points or softening points (the resin with the relatively high melting point or softening point being referred to as the "high-melting-point resin" and the resin with the relatively low one being referred to as the "low-melting-point resin"), wherein the low-melting-point resin is present continuously in the lengthwise direction of at least portions of the fiber surfaces. The high-melting-point resin is the component that expresses heat extensibility while the low-melting-point resin is the component that expresses heat sealability, and the heat-extendable composite fibers are able to undergo heat stretching at temperatures lower than the melting point of the high-melting-point resin component.

The types of high-melting-point resin and low-melting-point resin are not particularly restricted so long as they are capable of forming fibers. The melting point difference or softening point difference between the high-melting-point resin and low-melting-point resin will usually be 20° C. or higher, and is preferably 25° C. or higher.

The melting points of the high-melting-point resin and low-melting-point resin may be the melting points measured by the following method, for example. A differential scanning calorimeter (such as a DSC6200 by Seiko Instruments, Inc.) is used for thermal analysis of a finely cut fiber sample (for example, a 2 mg sample) at a temperature-elevating rate of 10° C./min, and the melting peak temperature of each resin is measured, defining the measured melting peak temperature as the melting point. When the melting point of the resin cannot be precisely measured by this method, the temperature at which the resin fuses to an extent allowing the fusion point strength of the fibers to be measured as the temperature at which molecular flow of the resin begins, is recorded as the softening point, and is used instead of the melting point.

The orientation index of the high-melting-point resin and low-melting-point resin can be appropriately adjusted by the type of resin. For example, when polypropylene is used as the high-melting-point resin, the orientation index is usually 60% or less, preferably 40% or less and even more preferably 25% or less. When a polyester is used as the high-melting-point resin, the orientation index is usually 25% or less, preferably 20% or less and even more preferably 10% or less. In contrast, the orientation index of the low-melting-point resin is usually 5% or greater, preferably 15% or greater and even more preferably 30% or greater. If the orientation indexes of the high-melting-point resin and the low-melting-point resin are within these ranges, the heat-extendable composite fibers will be able to efficiently elongate by heat treatment.

The orientation indexes of the high-melting-point resin and low-melting-point resin are indicators of the extent of orientation of the polymer chains of the resin composing the fibers, and they are calculated by the following formula.

Orientation index (%)=$X/Y$×100

[In the formula, X is the value of the birefringence of the resin in the heat-extendable composite fibers, and Y is the value of the intrinsic birefringence of the resin.]

The birefringence of the resin in the heat-extendable composite fibers (X in the above formula) is measured, for example, with a polarizing plate mounted on an interference microscope, under polarized light in the directions parallel to and perpendicular to the fiber axis. The dipping solution used may be, for example, a standard refraction liquid by Cargille Co. The refractive index of the dipping solution is measured using an Abbe refractometer, for example. Using the interference pattern of the composite fibers obtained by the interference microscope, the refractive index in the directions parallel and perpendicular to the fiber axis are determined based on a known method (for example, Journal of the Society of Fiber Science and Technology, Japan, "Fiber structure formation in high-speed spinning of core-sheath composite fibers", Vol. 51, No. 9, p. 408, 1995), and the birefringence is calculated as the difference between them.

The intrinsic birefringence of the resin (Y in the above formula) is the birefringence with the polymer chains of the resin in a completely oriented state, the values being listed, for example, in "Plastic materials in polymer processing", 1st Edition, Appendix table: "Typical materials used in polymer processing" (ed. Japan Society of Polymer Processing, Sigma Publishing, Feb. 10, 1998).

The heat stretching factor of heat-extendable composite fibers at a temperature of 10° C. higher than the melting point or softening point of the low-melting-point resin is preferably 0.5 to 20%, even more preferably 3 to 20% and yet more preferably 7.5 to 20%. As a result, the first layer 21 is bulky due to extension of the heat-extendable composite fibers, and a significantly irregular structure is formed on the skin contact surface of the first layer 21.

The heat stretching factor used is, for example, the heat stretching factor measured by the following method. Parallel aligned fibers are mounted in a TMA-50 thermomechanical analyzer (product of Shimadzu Corp.) with a chuck distance of 10 mm, and the temperature is increased at a temperature-elevating rate of 10° C./min under a fixed load of 0.025 mN/tex. The change in elongation percentage of the fibers at this time is measured, and the elongation percentage at the melting point or softening point of the low-melting-point resin, or the elongation percentage at a temperature 10° C. higher than the melting point or softening point of the low-melting-point resin, are read off and recorded as the heat stretching factor at each temperature. The reason for measuring the heat stretching factor in the aforementioned temperature range is that when the fiber intersections are heat fused, it is common to employ a range of at least the melting point or softening point of the low-melting-point resin, up to a temperature of about 10° C. higher.

The heat-extendable composite fibers may be core-sheath (concentric type or eccentric type) or side-by-side fibers. For core-sheath composite fibers, the sheath component and the core component may be composed of a low-melting-point resin and a high-melting-point resin, respectively. Examples for the core component include polypropylene (PP), polyethylene terephthalate (PET) and polybutylene terephthalate (PBT). When the core component is PP, examples for the sheath component include polyethylene (PE), such as high-density polyethylene (HDPE), low-density polyethylene (LDPE) and linear low-density polyethylene (LLDPE), as well as ethylene-propylene copolymer, polystyrene and the like. When the core component is PET, PBT or the like, the sheath component may be, for example, PP, copolymerized polyester or the like.

The ratio (weight ratio) of the low-melting-point resin with respect to the high-melting-point resin in the heat-extendable composite fibers may be appropriately adjusted in consideration of heat-extensibility, heat sealability and dynamic properties of the fibers, and it is usually 10:90 to 90:10, preferably 20:80 to 80:20 and more preferably 50:50 to 70:30.

The thickness of the heat-extendable composite fibers may be adjusted to 1.0 to 10 dtex (especially 1.7 to 8.0 dtex), for example, and the fiber lengths of the heat-extendable composite fibers may be adjusted to about 30 to 70 mm, for example.

Heat-extendable composite fibers having the desired heat stretching factor can be produced, for example, by heat treatment or crimping treatment of the spun composite fibers, without stretching treatment.

The conditions for heat treatment of the spun composite fibers can be appropriately adjusted according to the type of high-melting-point resin and low-melting-point resin composing the composite fibers. For example, with core-sheath composite fibers wherein the core component is polypropylene and the sheath component is high-density polyethylene, the heating temperature is usually 50° C. to 120° C. and preferably 70° C. to 100° C., while the heating time is usually 10-500 seconds and preferably 20-200 seconds. Examples for the heating medium include hot air and infrared rays.

The crimping treatment carried out on the spun composite fibers may be machine-texturing, for example. The crimping may be in either two-dimensional or three-dimensional mode, and it may be three-dimensional latent crimping seen with eccentric type core-sheath composite fibers and side-by-side composite fibers. When machine-texturing is accompanied by heat, the heat treatment and crimping treatment may be carried out simultaneously.

Incidentally, although the fibers will sometimes be elongated by crimping treatment, such elongation is not included by "stretching treatment". The term "stretching treatment" usually refers to stretching of unstretched filaments at a draw ratio of about 2 to 6.

The heat-extendable fiber layer 21' may also contain other fibers in addition to the heat-extendable fibers. Examples for other fibers include heat-sealable fibers and non-heat-extendable fibers. The heat-extendable fibers in the heat-extendable fiber layer 21' may also have a heat sealable property. When the heat-extendable fiber layer 21' contains other fibers, the content of the heat-extendable fibers may be appropriately adjusted in consideration of formability, bulk and compressive deformation of the projections 8, but it will usually be 50 mass % or greater and preferably 70 to 90 mass % of the heat-extendable fiber layer 21'.

From the viewpoint of increasing the concealing property of the top sheet 2, the heat-extendable fiber layer 21' may also contain an inorganic filler, such as titanium oxide, barium sulfate or calcium carbonate.

The thickness and basis weight of the heat-extendable fiber layer 21' may be appropriately adjusted in consideration of formability, bulk and compressive deformation of the projections 8, but the thickness will usually be 1 to 20 mm and preferably 0.2 to 10 mm, and the basis weight will usually be 5 to 80 g/m$^2$ and preferably 10 to 40 g/m$^2$.

The non-heat-extendable fiber layer 22' is a layer containing one or more different non-heat-extendable fibers. The non-heat-extendable fibers may be fibers having essentially no heat extensibility, or they may be fibers having heat extensibility but having a higher heat stretching initiation temperature than the heat stretching initiation temperature of the heat-extendable fibers in the heat-extendable fiber layer 21' (that is, fibers that essentially do not undergo heat stretching at a temperature below the heat stretching initiation temperature of the heat-extendable fibers in the heat-extendable fiber layer 21').

Examples of non-heat-extendable fibers include regenerated fibers, such as rayon; semisynthetic fibers, such as acetate; natural fibers, such as cotton and wool; and thermoplastic resin fibers, such as polyolefins (for example, polyethylene and polypropylene), polyesters (for example, polyethylene terephthalate) and polyamides. Non-heat-extendable fibers may also be core-sheath composite fibers or side-by-side composite fibers, composed of a combination of two or more different thermoplastic resins. For example, in the case of fibers containing a polyethylene resin, and especially fibers containing a high-density polyethylene resin (density: 0.92 to 0.97 g/cm$^3$), it is possible to obtain a softer feel. The size of the non-heat-extendable fibers can be adjusted to 0.5 to 20 dtex (especially 1.0 to 10 dtex), for example.

The non-heat-extendable fiber layer 22' may also contain other fibers in addition to the non-heat-extendable fibers. Such other fibers may be heat-sealable fibers, for example. The non-heat-extendable fibers the non-heat-extendable fiber layer 22' may also have a heat sealable property. The non-heat-extendable fiber layer 22' may also contain heat-extendable fibers. When the non-heat-extendable fiber layer 22' contains other fibers, the content of the non-heat-extendable fibers may be appropriately adjusted, but it will usually be 50 mass % or greater and preferably 70 to 90 mass % of the non-heat-extendable fiber layer 22'.

From the viewpoint of increasing the concealing property of the top sheet 2, the non-heat-extendable fiber layer 22' may also contain an inorganic filler, such as titanium oxide, barium sulfate or calcium carbonate.

The thickness and basis weight of the non-heat-extendable fiber layer 22' may be appropriately adjusted in consideration of formability, bulk and compressive deformation of the projections 8, but the thickness will usually be 0.1 to 20 mm and preferably 0.2 to 10 mm, and the basis weight will usually be 5 to 80 g/m$^2$ and preferably 10 to 40 g/m$^2$.

Examples of heat-sealable fibers that may be contained in the heat-extendable fiber layer 21' and/or the non-heat-extendable fiber layer 22' include heat-sealable fibers composed of a thermoplastic resin, such as polyolefin, polyester or polyamide.

Examples of polyolefins include straight-chain low-density polyethylene (LLDPE), low-density polyethylene (LDPE), medium-density polyethylene (MDPE), high-density polyethylene (HDPE), polypropylene, polybutylene, and copolymers composed mainly of the foregoing (for example, ethylene-vinyl acetate copolymer (EVA), ethylene-ethyl acrylate copolymer (EEA), ethylene-acrylic acid copolymer (EAA) or an ethylene-propylene random copolymer (EP)). Polyethylene, and especially HDPE, is preferred from the viewpoint of thermal processing properties since it has a relatively low softening point of around 100° C., and also has low rigidity and a pliable feel.

Examples of polyesters include polyesters of straight-chain or branched polyhydroxyalkane acids up to C20, such as polyethylene terephthalate (PET), polytrimethylene terephthalate (PTT), polybutylene terephthalate (PBT), polylactic acid and polyglycolic acid, copolymers composed mainly thereof, and copolymerized polyesters composed mainly of alkylene terephthalates copolymerized with a small amount of another component. PET is preferred from the viewpoint of its elastic repulsion which allows formation of fibers and nonwoven fabrics with high cushioning properties, as well as from an economical viewpoint, since it can be commercially obtained at low cost.

Examples of polyamides include 6-nylon and 6,6-nylon.

The heat-sealable fibers may be composed of a single type of thermoplastic resin, or they may be composite fibers comprising two or more thermoplastic resins (for example, core-sheath composite fibers or side-by-side composite fibers). Heat-sealable fibers may be short staple fibers or long filaments. The thicknesses of the heat-sealable fibers may be adjusted to 1-7 dtex, for example.

The form of the fiber aggregates composing the heat-extendable fiber layer 21' and non-heat-extendable fiber layer 22' may be a web formed by a carding method; a nonwoven fabric formed by a heat fusion method, hydroentangling method, needle punching method, solvent bonding method, spunbond method or meltblown method, or a knitted fabric or the like. A web formed by a carding method is the fiber aggregate prior to formation of a nonwoven fabric. Such a web is one that has not been subjected to post-treatment applied to a carded web in a nonwoven fabric production process (for example, heat fusion treatment in an air-through method or calender method), and has its fibers very loosely entangled.

The compressed sections 5' are recesses formed by heat embossing treatment. Heat embossing treatment can be carried out using an embossing apparatus 220 as shown in FIG. 6. The embossing apparatus 220 has an upper roll 221 provided with a plurality of projections (not shown) on the outer peripheral surface, and a lower roll 222 having a smooth outer peripheral surface. The plurality of projections of the upper roll 221 are formed to correspond to the shape and arrangement pattern for the compressed sections 5', and the plurality of sections of the heat-extendable fiber layer 21' which are mutually separated by the projections, are heated while being compressed in the thickness direction of the heat-extendable fiber layer 21'. This results in formation of compressed sections 5' where the heat-extendable fiber layer 21' and non-heat-extendable fiber layer 22' are integrated in the thickness direction, which serve as recesses. The compressed sections 5' formed in this manner are compacted and have a smaller thickness and increased density compared to the other sections of the laminated sheet 2'.

The heat-extendable fiber layer 21' is partially compressed by compressed sections 5'. For this embodiment, the sections of the heat-extendable fiber layer 21' compressed by the compressed sections 5' are bonded to the non-heat-extendable fiber layer 22', but they do not need to be bonded to the non-heat-extendable fiber layer 22'. Specifically, the compressed sections 5' may be formed in such a manner as to bond the heat-extendable fiber layer 21' and non-heat-extendable fiber layer 22', so long as the constituent fibers of the heat-extendable fiber layer 21' are bonded together in the thickness direction, or they may be formed in such a manner that both layers are not bonded. In this case, the heat-extendable fiber layer 21' and non-heat-extendable fiber layer 22' may be bonded by joining sections. The joining sections bonding the heat-extendable fiber layer 21' and the non-heat-extendable fiber layer 22' may be formed by a bonding method, such as, for example, heat embossing, ultrasonic embossing, adhesive bonding or the like.

When the heat-extendable fiber layer 21' and/or non-heat-extendable fiber layer 22' is to comprise heat-sealable fibers, melting and solidification of the heat-sealable fibers during formation of the compressed sections 5' can cause heat fusion of the heat-extendable fiber layer 21' and the non-heat-extendable fiber layer 22'. When the heat-sealable fibers are composite fibers, melting and solidification of the low-melting-point resin (for example, the resin of the sheath component of core-sheath composite fibers) can cause heat fusion of the heat-extendable fiber layer 21' and the non-heat-extendable fiber layer 22'.

The upper roll 221 and/or lower roll 222 may be heated in the embossing apparatus 220, allowing heating to be performed during compression. The heating temperature for embossing treatment by the embossing apparatus 220 will usually be 60° C. to 180° C. and is preferably 80° C. to 160° C., the pressure will usually be 10 to 3000 N/mm and is preferably 0.005 to 2 N/mm, and the treatment time will usually be 0.0001 to 5 seconds and is preferably 0.005 to 2 seconds.

The compressed sections 5' are roughly circular shapes, when the laminated sheet 2' is viewed flat from the heat-extendable fiber layer 21' side, and are disposed in a zigzag lattice-like fashion throughout. The compressed sections 5' may also be shapes other than circular shapes, such as ellipsoid, triangular, rectangular or polygonal. The arrangement pattern of the compressed sections 5' may be changed as appropriate, and for example, they may be continuously formed in a linear fashion with straight lines, curves or the like.

The number and locations of the compressed sections 5' may be adjusted as appropriate, in consideration of formability and bulk of the projections 8. One region surrounded by a plurality of compressed sections 5' (four compressed sections 5' for this embodiment) on the heat-extendable fiber layer 21' bulges out toward the skin contact surface side, starting from the compressed sections 5', thus forming one projection 8. The number of compressed sections 5' surrounding one region in which one projection 8 is formed will usually be 3 or more, and is preferably 4 or more. The upper limit will usually be 12, and is preferably 8.

A region in which one projection 8 is formed may be surrounded by compressed sections 5' continuously formed in a linear fashion by straight lines, curves or the like. For example, when the compressed sections 5' are formed in a mesh-like manner, the regions in the interior area of each mesh cell bulge toward the skin contact surface side, forming one projection 8. In this case, the compressed sections 5' preferably encompass 10-100% and more preferably encompass 20-100% of the total surrounding area of the region in which each projection 8 is formed.

Heat stretching treatment of the laminated sheet 2' can be carried out in the heat stretching treatment zone 170, such as shown in FIG. 6. A mesh conveyor belt, pin tenter, clip tenter or the like may be used to convey the laminated sheet 2' to the heat stretching treatment zone 170. When the laminated sheet 2' is transported in the heat stretching treatment zone 170, hot air heated to a temperature above the heat stretching initiation temperature of the heat-extendable fiber in the heat-extendable fiber layer 21' is blasted onto the laminated sheet 2', and the heat-extendable fiber layer 21' undergoes heat stretching.

The hot air blasting can be accomplished with an air-through system, for example. When the heat-extendable fibers in the heat-extendable fiber layer 21' are heat-extendable composite fibers, preferably the temperature of the hot air is set to a temperature that allows heat stretching of the heat-extendable composite fibers and heat fusion between the heat-extendable composite fibers; so as to cause heat fusion of the heat-extendable composite fibers that are in a free state.

The heat stretching factor of the heat-extendable fiber layer 21' can be appropriately adjusted by controlling the laminated sheet 2' transport speed and the hot air temperature and wind speed, and adjusting the tenter width.

Hot air blasting is merely an example of heat stretching treatment. The heat stretching treatment is not particularly restricted so long as it allows heating to above the heat stretching initiation temperature of the heat-extendable fibers. The heat stretching treatment can be carried out using hot air, or another heating medium, such as microwaves, steam or infrared rays.

The heating temperature and heating time for heat stretching treatment can be appropriately adjusted based on the heat stretching initiation temperature of the heat-extendable fiber. Details regarding heat stretching treatment are described, for example, in Japanese Unexamined Patent Publication No. 2005-350836, Japanese Unexamined Patent Publication No. 2010-168715 and Japanese Unexamined Patent Publication No. 2012-5701.

When the laminated sheet 2' is subjected to heat stretching treatment, as shown in FIG. 4, the heat-extendable fiber layer 21' deforms due to heat stretching of the heat-extendable fibers. Specifically, one region surrounded by a plurality of compressed sections 5' (four compressed sections 5' for this embodiment) on the heat-extendable fiber layer 21' bulges out toward the skin contact surface side, starting from the compressed sections 5', as heat stretching of the heat-extendable fibers takes place, thus forming one projection 8. Since numerous regions surrounded by a plurality of compressed sections 5' (four compressed sections 5' for this embodiment) are present in the heat-extendable fiber layer 21', deformation of the heat-extendable fiber layer 21' results in formation of numerous projections 8. Thus, numerous projections 8 are formed bulging to the skin contact surface side, produced by deformation of the heat-extendable fiber layer 21' at least in the excretory opening contact region 20 of the skin contact surface.

The heat-extendable fiber layer 21' and the non-heat-extendable fiber layer 22' after heat stretching treatment correspond to the first layer 21 and second layer 22, respectively. The first layer 21 is a layer wherein the heat-extendable fiber layer 21' partially compressed at the compressed sections 5' has undergone heat stretching, and it contains heat-stretched heat-extendable fibers, such as fibers whose actual fiber lengths have been extended by heat treatment (for example, fibers wherein the resin crystal state has been altered so that the actual fiber lengths are extended), or fibers whose actual fiber lengths have not been extended but whose apparent fiber lengths have been extended by heat treatment (for example, crimped fibers wherein developed zigzag, Ω-shaped or spiral-shaped crimping has been released such that the apparent fiber lengths are extended). The second layer 22 contains non-heat-extendable fibers that essentially have not been subjected to heat stretching.

The thickness and basis weight of the first layer 21 will vary depending on the thickness and basis weight of the heat-extendable fiber layer 21', but the thickness will usually be 0.2 to 10 mm and is preferably 0.4 to 2.5 mm, and the basis weight will usually be 5 to 80 g/m² and is preferably 10 to 40 g/m².

The thickness and basis weight of the second layer 22 will vary depending on the thickness and basis weight of the non-heat-extendable fiber layer 22', but the thickness will usually be 0.2 to 10 mm and is preferably 0.4 to 2.5 mm, and the basis weight will usually be 5 to 80 g/m² and is preferably 10 to 40 g/m².

The density of the second layer 22 is preferably greater than the density of the first layer 21. This can improve migration of menstrual blood from the first layer 21 to the second layer 22.

When the density of the second layer 22 is greater than the density of the first layer 21, the density of the second layer 22 is preferably 0.1 g/cm³ or less and more preferably 0.08 g/cm³ or less. In this case, the function and effect of the blood slipping agent are effectively exhibited without being inhibited by the second layer 22. The lower limit for the density of the second layer 22 is preferably 0.04 g/cm³ and more preferably 0.06 g/cm³.

When the density of the second layer 22 is greater than the density of the first layer 21, the density of the first layer 21 is preferably 0.05 g/cm³ or less and more preferably 0.04 g/cm³ or less. In this case, the function and effect of the blood slipping agent are effectively exhibited without being inhibited by the first layer 21. The lower limit for the density of the first layer 21 is preferably 0.005 g/cm³ and more preferably 0.01 g/cm³.

The densities of the first layer 21 and second layer 22 are calculated by dividing the basis weights by the thicknesses.

The basis weight can be measured by the following method, for example.

(1) A mark is created in the region to be measured and the area: $SA_\alpha$ (m²) is measured. In order to minimize error, marking is made so that the total area of the sample exceeds 5 cm².

(2) The marked area is cut with a sharp blade, for example a cutter replacement blade, and the total mass measured as TM (g).

(3) The basis weight $BS_\alpha$ (g/m²) of the area to be measured is determined by the following formula:

$$BS_\alpha \text{ (g/m}^2\text{)} = TM \text{ (g)}/SA_\alpha \text{ (m}^2\text{)}.$$

The thickness can be measured by the following method, for example.

Measurement is performed using a thickness gauge (FS-60DS by Daiei Kagaku Seiki Mfg. Co., Ltd.), after pressing 5 different locations (444 mm measuring plane) for 10 seconds with a measuring pressure of 3 g/cm² (constant pressure).

When the top sheet 2 has one or more third layers between the first layer 21 and the second layer 22, the density of the third layer is preferably adjusted so that the density increases from the first layer 21 toward the second layer 22. This can improve migration of menstrual blood from the first layer 21 to the second layer 22.

As shown in FIG. 4, the first layer 21 and the second layer 22 are partially joined by compressed sections 5, corresponding to the compressed sections 5' after heat stretching treatment, and the compressed sections 5 serve as recesses 9. The shapes and arrangement pattern of the compressed sections 5' are not significantly altered after heat stretching treatment, the compressed sections 5 being roughly circular when the top sheet 2 is viewed flat from the first layer 21 side, and disposed in a zigzag lattice-like fashion throughout. The heat stretching treatment may slightly alter the shapes and structures of the compressed sections 5' in some cases. For example, it may cause extension or melting solidification of the fibers composing the compressed sections 5' in some cases.

The proportion of the area of the compressed sections 5 with respect to the area of the first layer 21 (the area ratio) will usually be 2.5 to 50% and is preferably 4 to 20%.

So long as a plurality of projections 8 are formed bulging toward the skin contact surface side, produced by deformation of the heat-extendable fiber layer 21' at least in the excretory opening contact region 20 of the skin contact surface, the structure of the top sheet 2 is not particularly restricted and may be appropriately modified.

For example, the non-heat-extendable fiber layer 22' may be changed to a heat-extendable fiber layer for the laminated sheet 2'. The heat-extendable fiber layer may be constructed in the same manner as the heat-extendable fiber layer 21'.

Figure 5:
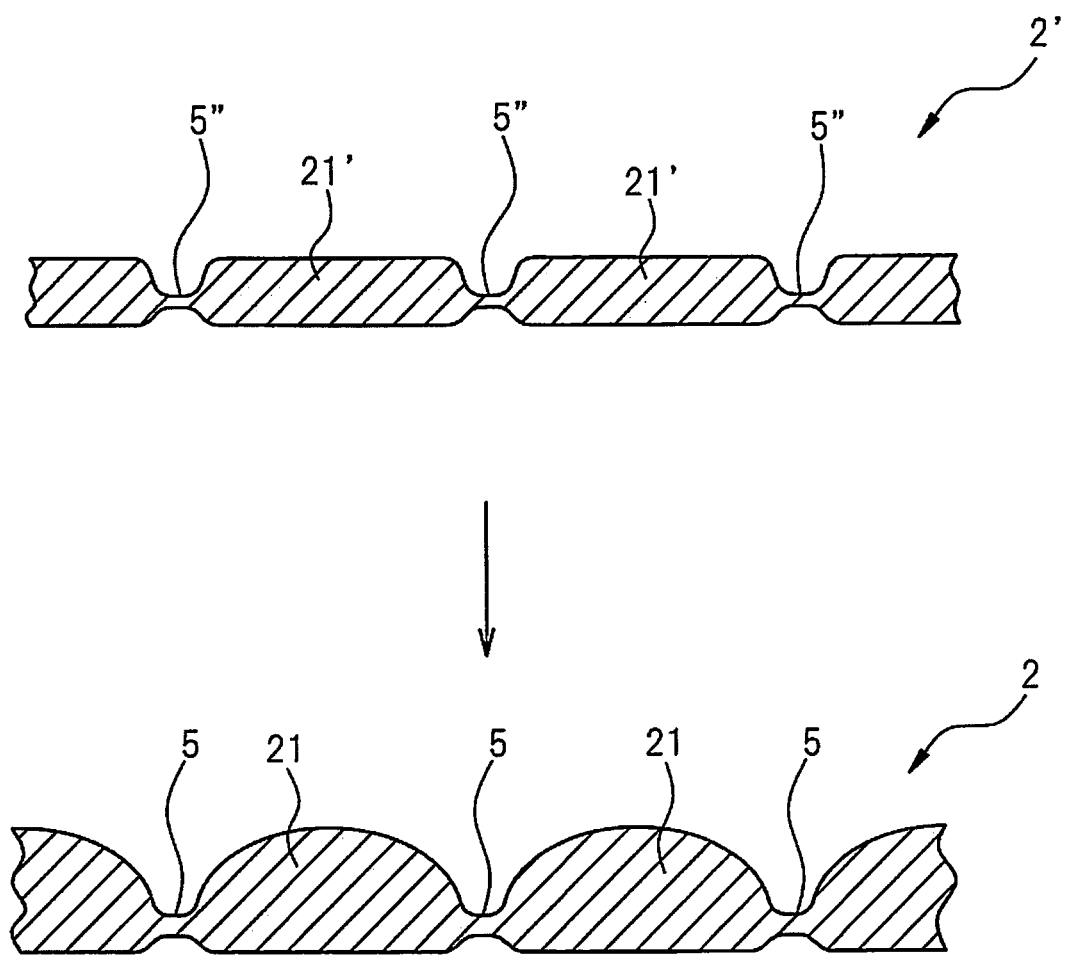
FIG. 5 is a partial magnified cross-sectional view showing the process by which a top sheet is produced by heat stretching treatment.

Also, the top sheet 2 may be a single-layer structure consisting of the first layer 21 alone. In this case, as shown in FIG. 5, the top sheet 2 is produced by heat stretching treatment of the heat-extendable fiber layer 21' partially compressed by the compressed sections 5'', and a plurality of projections 8 are formed by heat stretching of the heat-extendable fiber, similar to the laminated sheet 2'. The compressed sections 5'' are recesses formed by heat embossing treatment, similar to the compressed sections 5'. For heat embossing treatment, a plurality of mutually spaced locations of the heat-extendable fiber layer 21' are heated while being compressed in the thickness direction of the heat-extendable fiber layer 21', thereby causing compressed sections 5'', having the constituent fibers of the heat-extendable fiber layer 21' mutually integrated in the thickness direction, to be formed as recesses.

The first layer 21 and second layer 22 may also be bonded by the compressed sections 5. For example, after the first layer has been produced by heat stretching treatment of the heat-extendable fiber layer 21' that has been partially compressed by the compressed sections 5'', as shown in FIG. 5, the second layer may be layered to produce a top sheet 2 without the first layer 21 and second layer 22 bonded by compressed sections 5.

The top sheet 2 may also have one or more third layers in addition to the first layer 21 and the second layer 22. So long as the second layer 22 is provided on the non-skin contact surface side of the first layer 21, there are no particular restrictions on the location where the third layer is provided. For example, one or more third layers may be provided between the first layer 21 and the second layer 22. Alternatively, one or more third layers may be provided on the side of the second layer 22 opposite the first layer 21 side. The third layer may be a non-heat-extendable fiber layer or a heat-extendable fiber layer. Furthermore, so long as it does not interfere with the deformation of the heat-extendable fiber layer 21' that occurs with heat stretching of the heat-extendable fibers (especially bulging to the skin contact surface side), the third layer may have another layer in addition to the fiber layer (for example, an adhesive layer).

A plurality of open holes may also be provided in the top sheet 2. This will increase the liquid permeability and reduce leakage and mustiness. The open holes can be formed by perforating the top sheet 2, for example. The diameters of the open holes can be adjusted to 0.2 to 10 mm, for example. When a plurality of open holes are formed, the spacing between the open holes may be adjusted to 0.5 to 20 mm, for example.

The top sheet 2 may also be subjected to hydrophilicizing treatment. Hydrophilicizing treatment may be, for example, coating of the surface of the top sheet 2 with a hydrophilic agent, or addition of a hydrophilic agent to the constituent components of the first layer 21 and/or second layer 22, corona treatment, plasma treatment, or the like. When the top sheet 2 is subjected to hydrophilicizing treatment, lipophilic regions created by the blood slipping agent and hydrophilic regions created by the hydrophilic agent become sparsely dispersed in the top sheet 2, so that menstrual blood will tend to slip from the projections 8 of the top sheet 2 and migrate into the absorbent body.

The back sheet 3 is a sheet that prevents permeation of liquid excreta, such as menstrual blood, an example thereof being a liquid-impermeable layer. The back sheet 3 can prevent leakage of absorbed liquid excreta into the absorbent body 4. The one side of the back sheet is the side that contacts with the clothing (underwear) of the wearer. The back sheet 3 is preferably moisture-permeable in addition to being liquid-impermeable, in order to reduce mustiness during wear.

Examples for the back sheet 3 include waterproof treated nonwoven fabrics, films of synthetic resins (such as polyethylene, polypropylene and polyethylene terephthalate), composite sheets comprising nonwoven fabrics and synthetic resin films (such as composite films having an air permeable synthetic resin film bonded to a spunbond or spunlace nonwoven fabric), and SMS nonwoven fabrics comprising a highly water-resistant meltblown nonwoven fabric sandwiched between high-strength spunbond nonwoven fabrics.

The absorbent body 4 contains an absorbent material that absorbs liquid excreta, such as menstrual blood. The absorbent material contained in the absorbent body 4 is not particularly restricted so long as it can absorb and hold liquid excreta, such as menstrual blood. The absorbent material may be, for example, water-absorbent fibers or a high-water-absorbing material (for example, a high-water-absorbent resin or high-water-absorbent fibers). The absorbent body 4 may also contain additives, such as antioxidants, light stabilizers, ultraviolet absorbers, neutralizers, nucleating agents, epoxy stabilizers, lubricants, antimicrobial agents, flame retardants, antistatic agents, pigments or plasticizers, as necessary.

Examples of water-absorbent fibers include wood pulp obtained using a conifer or broadleaf tree material as the starting material (for example, mechanical pulp, such as groundwood pulp, refiner ground pulp, thermomechanical pulp and chemithermomechanical pulp; chemical pulp, such as Kraft pulp, sulfide pulp and alkaline pulp; and semichemical pulp); mercerized pulp or crosslinked pulp obtained by chemical treatment of wood pulp; nonwood pulp, such as bagasse, kenaf, bamboo, hemp and cotton (for example, cotton linter); regenerated cellulose, such as rayon and fibril rayon; and semi-synthetic celluloses, such as acetates and triacetates, among which ground pulp is preferred from the viewpoint of low cost and easy shaping.

Examples of high-water-absorbing materials include starch-based, cellulose-based and synthetic polymer high-water-absorbing materials. Examples of starch-based or cellulose-based high-water-absorbing materials include starch-acrylic acid (acrylate) graft copolymer, saponified starch-acrylonitrile copolymer and crosslinked sodium carboxymethyl cellulose, and examples of synthetic polymer-based high-water-absorbing materials include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulose-based high water-absorbent resins (Superabsorbent Polymers: SAP), among which polyacrylic acid salt-based (especially sodium polyacrylate-based) high water-absorbent resins are preferred. Examples of high-water-absorbing material forms include particulate, filamentous and scaly forms, and in the case of particulates, the particle size is preferably 50 to 1000 μm and more preferably 100 to 600 μm.

When the absorbent body 4 contains a high-water-absorbing material (for example, a high-water-absorbing resin or high water-absorbent fibers), the content of the high-water-absorbing material will usually be 5 to 80 mass %, preferably 10 to 60 mass % and more preferably 20 to 40 mass % of the absorbent body 4.

The absorbent body 4 may also contain silver, copper, zinc, silica, active carbon, aluminosilicate compounds, zeolite, or the like. These can impart functions, such as deodorant, antibacterial or heat-absorbing effects to the absorbent body.

The thickness and basis weight of the absorbent body 4 can be appropriately adjusted according to the properties desired for the sanitary napkin 1 (for example, absorption property, strength and lightweight property). The thickness of the absorbent body 4 will usually be 0.1 to 15 mm, preferably 1 to 10 mm and more preferably 2 to 5 mm, and the basis weight will usually be 20 to 1000 g/m$^2$, preferably 50 to 800 g/m$^2$ and more preferably 100 to 500 g/m$^2$. The thickness and basis weight of the absorbent body 4 may be constant across the entire absorbent body 4, or it may partially differ.

The absorbent body 4 may have a core containing an absorbent material, and a core wrap covering the core. The core wrap is not particularly restricted so long as it has liquid permeability and absorbent body retentivity. Examples for the core wrap include nonwoven fabrics, woven fabrics, liquid permeation hole-formed synthetic resin films and meshed net-like sheets, among which tissues formed by a wet method using ground pulp as the main material are preferred from the viewpoint of low cost.

In addition to the top sheet 2, the sanitary napkin 1 may be provided with a second sheet positioned between the top sheet 2 and the absorbent body 4, as a liquid-permeable layer. In this case, a blood slipping agent may be coated onto the second sheet.

The second sheet is not particularly restricted so long as it allows passage of liquid excreta, such as menstrual blood, and the second sheet thickness, basis weight, density and other properties may be appropriately adjusted within ranges that allow passage of liquid excreta, such as menstrual blood.

Examples for the second sheet include nonwoven fabrics, woven fabrics, liquid permeation hole-formed synthetic resin films and meshed net-like sheets. Examples of nonwoven fabrics include air-through nonwoven fabrics, spunbond nonwoven fabrics, point bond nonwoven fabrics, spunlace nonwoven fabrics, needle punching nonwoven fabrics, meltblown nonwoven fabrics, and their combinations (such as SMS), and examples of fibers to compose the nonwoven fabrics include natural fibers (wool, cotton and the like), regenerated fibers (rayon, acetate and the like), inorganic fibers (glass fiber, carbon fibers and the like), synthetic resin fibers (polyolefins, such as polyethylene, polypropylene, polybutylene, ethylene-vinyl acetate copolymer, ethylene-ethyl acrylate copolymer, ethylene-acrylic acid copolymer and ionomer resins; polyesters, such as polyethylene terephthalate, polybutylene terephthalate, polytrimethylene terephthalate and polylactic acid; and polyamides, such as nylon). The nonwoven fabric may be combined with composite fibers, such as core/sheath fibers, side-by-side fibers and sea/island fibers, hollow type fibers; irregularly shaped fibers, such as flat fibers, Y-shaped fibers or C-shaped fibers; solid crimped fibers, such as latent crimped or developed crimped fibers, or split fibers that have been split by a physical load, such as a water stream, heat, embossing or the like.

<Method for Producing Absorbent Article>

An embodiment of a method for producing an absorbent article according to the invention will now be described, using a method for producing a sanitary napkin 1 as an example.

The production method according to this embodiment comprises a step of forming an absorbent body (step 1), a step of layering a top sheet on the absorbent body (step 2), a step of layering a back sheet (step 3), a step of cutting out a sanitary napkin (step 4) and a step of coating the sanitary napkin with a blood slipping agent (step 5), and the production apparatus 100 shown in FIG. 6 is used.

[Step 1]

Recesses 124 are formed at a prescribed pitch in the circumferential direction on the peripheral surface of a suction drum 120 rotating in the machine direction MD, as a molding form in which the absorbent body material 122 is to be packed. When the suction drum 120 is rotated and the recesses 124 approach the material feeder 121, the suction section 126 acts on the recesses 124 and the absorbent body material 122 supplied from the material feeder 121 is vacuum suctioned into the recesses 124. The material feeder 121 is formed to cover the suction drum 120, and the material feeder 121 supplies the absorbent body material 122 into the recesses 124 by air transport, forming an absorbent body 4 in the recesses 124. The absorbent body 4 formed in the recesses 124 is transferred onto a carrier sheet 110 advancing in the machine direction MD.

[Step 2]

The top sheet 2 is layered on the absorbent body 4, forming a layered body 262.

Next, compressed grooves are formed if necessary in the layered body 262. Compressed grooves are formed using an embossing apparatus 130. The embossing apparatus 130 has an upper roll 131 provided with projections (not shown) on the outer peripheral surface, and a lower roll 132 having a smooth outer peripheral surface. The projections of the upper roll 131 are formed to correspond to the shapes and arrangement pattern of the compressed grooves. When the layered body 262 passes between the upper roll 131 and lower roll 132 of the embossing apparatus 130, the layered body 262 becomes compressed in the thickness direction, and compressed grooves are formed in the layered body 262. The compressed grooves are formed on the top sheet 2 around the excretory opening contact region 20 or in the surrounding region of the excretory opening contact region 20. Formation of compressed grooves integrate the top sheet 2 with the absorbent body 4. When the step of forming the compressed grooves with the embossing apparatus 130 is unnecessary, it may be omitted.

[Step 3]

The back sheet 3 supplied from the back sheet roll 140 is layered on the surface of the lower side of the layered body 134 (the side opposite the top sheet) via an adhesive layer, to form a continuous section 144 of the sanitary napkin. When the step of forming compressed grooves with an embossing apparatus 130 is omitted, the layered body 134 and the layered body 262 are identical.

[Step 4]

A cutter 150 is used to cut the continuous section 144 of the sanitary napkin, thereby cutting out a sanitary napkin.

[Step 5]

A blood slipping agent 161 is coated onto the top sheet 2 of the sanitary napkin using spray 160, thereby forming a blood slipping agent layer on the surface of the top sheet 2. The blood slipping agent layer is formed in at least the excretory opening contact region 20 on the skin contact surface of the top sheet 2.

For this embodiment, the blood slipping agent was coated after cutting out the sanitary napkin, but it may instead be coated at any stage before cutting, or it may be coated during the production steps for the top sheet. In order to prevent dripping down of the blood slipping agent that has been coated during production, the blood slipping agent is preferably coated at a downstream stage of the production process, such as immediately before packaging of the sanitary napkin.

The method for producing the sanitary napkin 1 may comprise, in addition to steps 1 to 5, also a step of forming seal sections 7a, 7b, 8a, 8b and a step of forming pressure-sensitive adhesive sections 9a, 9b, 9c.

<Blood Slipping Agent>

The blood slipping agent has a kinematic viscosity of about 0.01 to about 80 $mm^2/s$ at 40° C., a water holding percentage of about 0.05 to about 4.0 mass %, and a weight-average molecular weight of less than about 1,000.

The 40° C. kinematic viscosity of the blood slipping agent may be appropriately adjusted in the range of about 0 to about 80 $mm^2/s$, but it is preferably about 1 to about 70 $mm^2/s$, more preferably about 3 to about 60 $mm^2/s$, even more preferably about 5 to about 50 $mm^2/s$ and yet more preferably about 7 to about 45 $mm^2/s$. As used herein, the "40° C. kinematic viscosity" may be referred to simply as "kinematic viscosity".

The kinematic viscosity tends to be higher with a) a larger molecular weight of the blood slipping agent, b) a higher percentage of polar groups, such as carbonyl bonds (—CO—), ether bonds (—O—), carboxyl groups (—COOH) and hydroxyl groups (—OH), and c) a larger IOB.

In order to have a kinematic viscosity of about 0 to about 80 mm$^2$/s at 40° C., the melting point of the blood slipping agent is preferably no higher than 45° C. This is because the kinematic viscosity will tend to be higher if the blood slipping agent contains crystals at 40° C.

The significance of the kinematic viscosity of the blood slipping agent will be explained below, but a kinematic viscosity exceeding about 80 mm$^2$/s will tend to result in high viscosity of the blood slipping agent, such that it will not as easily slip down from the projections to the recesses together with menstrual blood that has reached the skin contact surface of the top sheet, and subsequently migrate into the absorbent body.

The kinematic viscosity can be measured according to JIS K 2283:2000, "5. Kinematic Viscosity Test Method", using a Cannon-Fenske reverse-flow viscometer, at a testing temperature of 40° C.

The water holding percentage of the blood slipping agent may be appropriately adjusted in the range of about 0.01 to about 4.0 mass %, but it is preferably about 0.02 to about 3.5 mass %, more preferably about 0.03 to about 3.0 mass %, even more preferably about 0.04 to about 2.5 mass % and yet more preferably about 0.05 to about 2.0 mass %.

As used herein, "water holding percentage" means the percentage (mass) of water that can be held by a substance, and it may be measured in the following manner.

(1) A 20 mL test tube, a rubber stopper, the substance to be measured and deionized water are allowed to stand for a day and a night in a thermostatic chamber at 40° C.

(2) Into the test tube in the thermostatic chamber there are charged 5.0 g of the substance to be measured and 5.0 g of deionized water.

(3) The mouth of the test tube is closed with the rubber stopper in the thermostatic chamber, and the test tube is rotated once and allowed to stand for 5 minutes.

(4) A 3.0 g portion of the layer of the substance to be measured (usually the upper layer) is sampled into a glass dish with a diameter of 90 mm and a mass of $W_0$ (g), in the thermostatic chamber.

(5) The dish is heated at 105° C. for 3 hours in an oven to evaporate off the moisture, and the mass $W_1$ (g) of each dish is measured.

(6) The water holding percentage is calculated by the following formula.

$$\text{Water holding percentage (mass \%)} = 100 \times [W_0 (g) - W_1 (g)]/3.0 (g)$$

The measurement is conducted three times, and the average value is recorded.

The significance of the water holding percentage of the blood slipping agent will be explained below, but a low water holding percentage will tend to lower the affinity between the blood slipping agent and menstrual blood, thus impeding its migration into the absorbent body together with menstrual blood that has reached the skin contact surface of the top sheet. If the water holding percentage is high, on the other hand, the affinity between menstrual blood and the blood modifying agent will become very high, similar to a surfactant, and absorbed menstrual blood will tend to remain on the skin contact surface of the top sheet, resulting in more red coloration of the skin contact surface of the top sheet.

The water holding percentage tends to be a larger value with a) a smaller molecular weight of the blood slipping agent, and b) a higher percentage of polar groups, such as carbonyl bonds (—CO—), ether bonds (—O—), carboxyl groups (—COOH) and hydroxyl groups (—OH). This is because the blood slipping agent has greater hydrophilicity. The water holding percentage will tend to have a larger value with a greater IOB, i.e. with a higher inorganic value or with a lower organic value. This is also because the blood slipping agent has greater hydrophilicity.

The significance of the kinematic viscosity and water holding percentage of the blood slipping agent will now be explained.

Menstrual blood excreted by the wearer and reaching the excretory opening contact region contacts the blood slipping agent in the projections and slips down together with it into the recesses, passing through the top sheet and migrating into the absorbent body.

More specifically, since the blood slipping agent with a kinematic viscosity of about 0.01 to about 80 mm$^2$/s at 40° C. has very low viscosity near the body temperature of the wearer and has a constant affinity with the menstrual blood, it slips down from the projections to the recesses together with the menstrual blood, and utilizing the energy during sliding, the menstrual blood is able to pass through the recesses of the top sheet to rapidly migrate into the absorbent body. Also, since the blood slipping agent present in the projections has a water holding percentage of about 0.01 to about 4.0 mass %, presumably it has no affinity with the hydrophilic component (blood plasma, etc.) in the menstrual blood, and therefore the menstrual blood does not easily remain on the top sheet.

When the menstrual blood discharged by the wearer is a large amount of menstrual blood, the menstrual blood easily migrates into the absorbent body, even when the kinetic energy of the menstrual blood itself is high and the kinematic viscosity of the blood slipping agent is relatively high so that it does not easily slip down together with the menstrual blood, or when the water holding percentage value is relatively high so that affinity with the hydrophilic components of the menstrual blood is high, or when the weight-average molecular weight value is relatively high so that it does not easily slip down together with the menstrual blood, or when the skin contact surface of the top sheet does not have an irregular structure.

When the menstrual blood discharged by the wearer is a small amount of menstrual blood, on the other hand, the kinetic energy of the menstrual blood is low, and menstrual blood that has reached the skin contact surface of the top sheet tends to easily pool in such cases. Consequently, the blood slipping agent slides down from the projections into the recesses together with the menstrual blood, and the menstrual blood is drawn into the top sheet and then drawn into the absorbent body, so that the menstrual blood can rapidly migrate into the absorbent body.

The blood slipping agent has a weight-average molecular weight of less than about 1,000, and preferably a weight-average molecular weight of less than about 900. This is because if the weight-average molecular weight is about 1,000 or higher, tack may be produced in the blood slipping agent itself, tending to create a feeling of discomfort for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor during wear.

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

The weight-average molecular weights used throughout the present specification are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 μL
Detection: RI (differential refractometer)

The weight-average molecular weights listed in the examples of the present specification were measured under the conditions described below.

The blood slipping agent may have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=Inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso branching | 0 | −10 |
| tert branching | 0 | −20 |
| Light metal (salt) | ≥500 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of no higher than 45° C., and more preferably it has a melting point of no higher than 40° C. If the blood slipping agent has a melting point of no higher than 45° C., the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood slipping agent has a melting point of no higher than about 45° C., it may be either liquid or solid at room temperature (about 25° C.), or in other words, the melting point may be either about 25° C. or higher or below about 25° C., and for example, it may have a melting point of about −5° C. or about −20° C.

The blood slipping agent does not have a lower limit for its melting point, but its vapor pressure is preferably low. The vapor pressure of the blood slipping agent is preferably between about 0 and about 200 Pa, more preferably between about 0 and about 100 Pa, more preferably between about 0 and about 10 Pa, even more preferably between about 0 and about 1 Pa and yet more preferably between about 0.0 and about 0.1 Pa, at 25° C. (1 atmosphere).

Considering that the absorbent article of the present disclosure is to be used in contact with the human body, the vapor pressure is preferably between about 0 and about 700 Pa, more preferably between about 0 and about 100 Pa, more preferably between about 0 and about 10 Pa, even more preferably between about 0 and about 1 Pa and yet more preferably between about 0.0 and about 0.1 Pa, at 40° C. (1 atmosphere). If the vapor pressure of the blood slipping agent is high, gasification may occur during storage and the amount may be reduced, often creating problems, such as odor during wear.

The melting point of the blood slipping agent may be selected depending on the weather or duration of wear. For example, in regions with a mean atmospheric temperature of no higher than about 10° C., using a blood slipping agent with a melting point of no higher than about 10° C. may help the blood slipping agent function after excretion of menstrual blood, even if it has been cooled by the ambient temperature.

Also, when the absorbent article is to be used for a prolonged period of time, the melting point of the blood slipping agent is preferably at the high end of the range of no higher than about 45° C. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, the top sheet coated with the surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, has low affinity with menstrual blood and therefore does not cause residue of menstrual blood on the top sheet and allows rapid migration into the absorbent body.

The blood slipping agent is preferably selected from the group consisting of the following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as "alkane"), an olefin-based hydrocarbon (containing one double bond, also referred to as "alkene"), an acetylene-based hydrocarbon (containing one triple bond, also referred to as "alkyne"), or a hydrocarbon or cyclic hydrocarbon comprising two or more bonds selected from the group consisting of double bonds or triple bonds, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include chain hydrocarbons and branched-chain hydrocarbons.

When two or more oxy groups (—O—) are inserted in the compounds of (ii) and (iii) above, the oxy groups (—O—) are not adjacent. Thus, compounds (ii) and (iii) do not include compounds with continuous oxy groups (i.e. peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

The blood slipping agent is more preferably selected from the group consisting of the following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety.

When 2 or more identical or different bonds are inserted in a compound of (ii') or (iii'), that is, when 2 or more identical or different bonds selected from among carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent more preferably has no more than about 1.8 carbonyl bonds (—CO—), no more than two ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

The blood slipping agent is even more preferably selected from the group consisting of the following items (A)-(F), and any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

The blood slipping agent according to (A) to (F) will now be explained in detail.

[(A) Ester of (A1) a Compound Having a Chain Hydrocarbon Moiety and 2-4 Hydroxyl Groups Substituting Hydrogens on the Chain Hydrocarbon Moiety, and (A2) a Compound Having a Chain Hydrocarbon Moiety and 1 Carboxyl Group Substituting a Hydrogen on the Chain Hydrocarbon Moiety]

The (A) ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety (hereunder also referred to as "compound (A)") does not need to have all of the hydroxyl groups esterified, so long as it has the aforementioned kinematic viscosity, water holding percentage and weight-average molecular weight.

Examples for the (A1) compound having a chain hydrocarbon moiety and 2-4 hydroxyl groups substituting at hydrogens of the chain hydrocarbon moiety (hereunder also referred to as "compound (A1)") include chain hydrocarbon tetraols, such as alkanetetraols including pentaerythritol, chain hydrocarbon triols, such as alkanetriols including glycerin, and chain hydrocarbon diols, such as alkanediols including glycols.

Compounds for the (A2) compound having a chain hydrocarbon moiety and one carboxyl group substituting at a hydrogen of the chain hydrocarbon moiety include compounds in which one hydrogen on the hydrocarbon is substituted with one carboxyl group (—COOH), such as fatty acids.

Examples for compound (A) include (a₁) an ester of a chain hydrocarbon tetraol and at least one fatty acid, (a₂) an ester of a chain hydrocarbon triol and at least one fatty acid, and (a₃) an ester of a chain hydrocarbon diol and at least one fatty acid.

[(a₁) Ester of a Chain Hydrocarbon Tetraol and at Least One Fatty Acid]

Examples of esters of a chain hydrocarbon tetraol and at least one fatty acid include tetraesters of pentaerythritols and fatty acids, represented by the following formula (1):

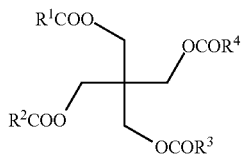
(1)

triesters of pentaerythritol and fatty acids, represented by the following formula (2):

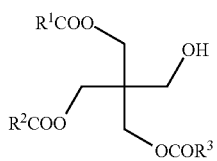
(2)

diesters of pentaerythritol and fatty acids, represented by the following formula (3):

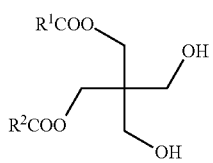
(3)

and monoesters of pentaerythritol and fatty acids, represented by the following formula (4).

(4)

(In the formulas, $R^1$ to $R^4$ each represent a chain hydrocarbon.)

The fatty acids composing the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of $R^1C$, $R^2C$, $R^3C$ or $R^4C$, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid (CO, decanoic acid ($C_{10}$), dodecanoic acid ($C_{12}$), tetradecanoic acid ($C_{14}$), hexadecanoic acid ($C_{16}$) heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$) and triacontanoic acid ($C_{30}$), as well as isomers of the foregoing that have not been mentioned.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$) elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid derived from a saturated fatty acid, or in other words, an ester of pentaerythritol and a saturated fatty acid.

Also, in order to lower the water holding percentage value, the ester of pentaerythritol and a fatty acid is preferably a diester, triester or tetraester, more preferably a triester or tetraester, and most preferably a tetraester.

From the viewpoint of the IOB being from about 0.00 to about 0.60, for a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

(5)

diesters of glycerin and fatty acids, represented by the following formula (6):

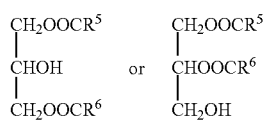
(6)

and monoesters of glycerin and fatty acids, represented by the following formula (7):

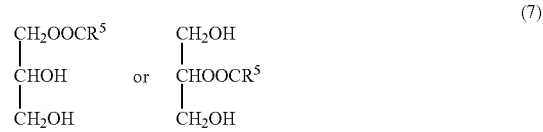
(7)

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of chain hydrocarbon tetraol and at least one fatty acid", namely saturated fatty acids and unsaturated fatty acids, and in consideration of the potential for degradation by oxidation and the like, the ester is preferably a glycerin and fatty acid ester derived from a saturated fatty acid, or in other words, an ester of glycerin and a saturated fatty acid.

Also, from the viewpoint of lowering the water holding percentage value, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid (CO and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

Considered from the viewpoint of obtaining a melting point of no higher than about 45° C., the triester of glycerin and a fatty acid preferably has a total number of carbon atoms in the fatty acid composing the triester of glycerin and a fatty acid, i.e. a total number of carbons in the $R^5C$, $R^6C$ and $R^7C$ portions in formula (5), of about 40 or less.

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of esters of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of esters of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2 to 6, and $R^8$ and $R^9$ each represent a chain hydrocarbon,
and monoesters of $C_2$-$C_6$ glycols and fatty acids, represented by the following formula (9):

$$R^8COOC_kH_{2k}OH \qquad (9)$$

wherein k represents an integer of 2 to 6, and $R^8$ is a chain hydrocarbon.

The fatty acid to be esterified in an ester of a $C_2$-$C_6$ glycol and a fatty acid (corresponding to $R^8COOH$ and $R^8COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^8C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage value, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage value, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting Hydrogens on the Chain Hydrocarbon Moiety and (B2) a Compound Having a Chain Hydrocarbon Moiety and 1 Hydroxyl Group Substituting a Hydrogen on the Chain Hydrocarbon Moiety]

The (B) ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety (hereunder also referred to as "compound (B)") does not need to have all of the hydroxyl groups etherified, so long as it has the aforementioned kinematic viscosity, water holding percentage and weight-average molecular weight.

The (B1) compound having a chain hydrocarbon moiety and 2-4 hydroxyl groups substituting at hydrogens of the chain hydrocarbon moiety (hereunder also referred to as "compound (B1)"), may be pentaerythritol, glycerin or glycol, for example, mentioned as compound (A1) for "compound (A)".

The (B2) compound having a chain hydrocarbon moiety and one hydroxyl group substituting at a hydrogen of the chain hydrocarbon moiety (hereunder also referred to as "compound (B2)") may be, for example, a compound in which one hydrogen of the hydrocarbon is substituted with one hydroxyl group (—OH), such as an aliphatic monohydric alcohol, which may be a saturated aliphatic monohydric alcohol or an unsaturated aliphatic monohydric alcohol.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein one C—C single bond of a saturated aliphatic monohydric alcohol mentioned above is replaced with a C═C double bond, such as oleyl alcohol, and for example, such alcohols are commercially available by New Japan Chemical Co., Ltd. as the RIKACOL Series and UNJECOL Series.

Examples for compound (B) include ($b_1$) ethers of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, (b₂) ethers of a chain hydrocarbon triol and at least one aliphatic monohydric alcohol, such as monoethers, diethers and triethers, preferably diethers and triethers and more preferably triethers, and (b₃) ethers of a chain hydrocarbon diol and at least one aliphatic monohydric alcohol, such as monoethers and diethers, and preferably diethers.

Examples of ethers of a chain hydrocarbon tetraol and at least one aliphatic monohydric alcohol include tetraethers, triethers, diethers and monoethers of pentaerythritol and aliphatic monohydric alcohols, represented by the following formulas (10) to (13):

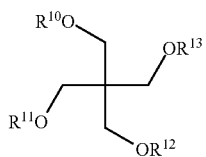 (10)

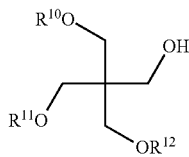 (11)

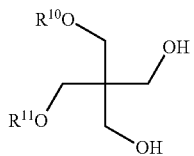 (12)

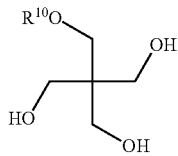 (13)

wherein $R^{10}$-$R^{13}$ each represent a chain hydrocarbon.

Examples of ethers of a chain hydrocarbon triol and at least one aliphatic monohydric alcohol include triethers, diethers and monoethers of glycerin and aliphatic monohydric alcohols, represented by the following formulas (14) to (16):

 (14)

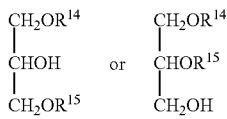 (15)

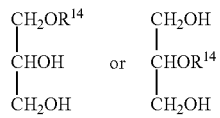 (16)

wherein $R^{14}$-$R^{16}$ each represent a chain hydrocarbon.

Ethers of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2 to 6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2 to 6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) can be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting Hydrogens on the Chain Hydrocarbon Moiety and (C2) a Compound Having a Chain Hydrocarbon Moiety and 1 Hydroxyl Group Substituting a Hydrogen on the Chain Hydrocarbon Moiety]

The (C) ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety (hereunder also referred to as "compound (C)") does not need to have all of the carboxyl groups esterified so long as it has the aforementioned kinematic viscosity, water holding percentage and weight-average molecular weight.

Examples for the (C1) carboxylic acid, hydroxy acid, alkoxy acid or oxoacid including a chain hydrocarbon moiety and 2-4 carboxyl groups substituting hydrogens of the chain hydrocarbon moiety (hereunder also referred to as "compound (C1)") include chain hydrocarbon carboxylic acids with 2-4 carboxyl groups, for example, chain hydrocarbon dicarboxylic acids, which include alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, which include alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, which include alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Also, compound (C1) includes chain hydrocarbon hydroxy acids with 2-4 carboxyl groups, for example, chain hydrocarbon alkoxy acids with 2-4 carboxyl groups, such as malic acid, tartaric acid, citric acid and isocitric acid, and O-acetylcitric acid or chain hydrocarbon oxoacids with 2-4 carboxyl groups.

The (C2) compound with a chain hydrocarbon moiety and one hydroxyl group substituting at a hydrogen of the chain hydrocarbon moiety may be any of those mentioned for "compound (B)", such as an aliphatic monohydric alcohol.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of aliphatic monohydric alcohols and aliphatic monohydric alcohols include compounds having the following formula (19):

$$R^{19}OR^{20} \qquad (19)$$

wherein $R^{19}$ and $R^{20}$ each represent a chain hydrocarbon.

The aliphatic monohydric alcohol composing the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of fatty acids and aliphatic monohydric alcohols include compounds having the following formula (21):

wherein $R^{23}$ and $R^{24}$ each represent a chain hydrocarbon.

Examples of fatty acids composing esters (corresponding to $R^{23}COOH$ in formula (21)) include the fatty acids mentioned for the "($a_1$) esters of chain hydrocarbon tetraols and fatty acids", and specifically these include saturated fatty acids and unsaturated fatty acids, with saturated fatty acids being preferred in consideration of the potential for degradation by oxidation and the like. The aliphatic monohydric alcohol composing the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

wherein $R^{25}$ and $R^{26}$ are each an alkyl group.

The dialkyl carbonate may be a commercially available product, or it may be synthesized by reaction between phosgene and an alcohol, reaction between a formate chloride ester and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, and ($d_4$) a dialkyl carbonate.

If the total number of carbon atoms is about 8 in a ($d_2$) dialkyl ketone, the melting point will be approximately −50° C. and the vapor pressure will be about 230 Pa at 20° C., in the case of 5-nonanone, for example.

[(E) Polyoxy $C_3$-$C_6$ Alkylene Glycol, or Alkyl Ester or Alkyl Ether Thereof]

The (E) polyoxy $C_3$-$C_6$ alkylene glycol, or its alkyl ester or alkyl ether (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

The polyoxy $C_3$-$C_6$ alkylene glycol is i) a homopolymer having one backbone selected from the group consisting of oxy $C_3$-$C_6$ alkylene backbones, i.e. oxyethylene backbone, oxypropylene backbone, oxybutylene backbone, oxypentylene backbone and oxyhexylene backbone, and having hydroxy groups at both ends, ii) a block copolymer having a backbone of two or more selected from among the aforementioned group and having hydroxy groups at both ends, or iii) a random copolymer having a backbone of two or more selected from among the aforementioned group and having hydroxy groups at both ends.

A polyoxy $C_3$-$C_6$ alkylene glycol is represented by the following formula (23):

wherein m is an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the ($e_1$) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n≥about 7 (when n=7, the IOB is 0.57).

Examples of commercial products of poly $C_3$-$C_6$ alkylene glycols include UNIOL™ PB-500 and PB-700 (all products of NOF Corp.).

[($e_2$) Ester of a Polyoxy $C_3$-$C_6$ Alkylene Glycol and at Least One Fatty Acid]

The ester of a polyoxy $C_3$-$C_6$ alkylene glycol and at least one fatty acid may be one wherein one or both of the OH ends of a polyoxy $C_3$-$C_6$ alkylene glycol mentioned above under "($e_1$) Polyoxy $C_3$-$C_6$ alkylene glycol" are esterified by a fatty acid, i.e. a monoester or a diester.

Examples of fatty acids to be esterified in the ester of a polyoxy $C_3$-$C_6$ alkylene glycol and at least one fatty acid include the fatty acids mentioned above under "($a_1$) Ester of chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

The ether of a polyoxy $C_3$-$C_6$ alkylene glycol and at least one aliphatic monohydric alcohol may be one wherein one or both of the OH ends of a polyoxy $C_3$-$C_6$ alkylene glycol mentioned above under "($e_1$) Polyoxy $C_3$-$C_6$ alkylene glycol" are etherified by an aliphatic monohydric alcohol, i.e. a monoether or diether.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include ($f_1$) chain alkanes, such as straight-chain alkanes and branched chain alkanes. Straight-chain alkanes with melting points of no higher than about 45° C. have up to about 22 carbon atoms, and at a vapor pressure of 1 atmosphere and about 0.01 Pa or less at 25° C., the number of carbon atoms is 13 or greater. Branched chain alkanes tend to have lower melting points than straight-chain alkanes, given the same number of carbon atoms. Branched chain alkanes may therefore include those with 22 and more carbon atoms, even with melting points of below about 45° C.

Examples of commercially available hydrocarbon products include PARLEAM 6 (NOF Corp.).

At least the projections 8 of the excretory opening contact region 20 may be coated with the blood slipping agent alone, or with a blood slipping agent-containing composition comprising the blood slipping agent and at least one other component.

Such a blood slipping agent-containing composition will now be described. Coating of the blood slipping agent-containing composition is the same as coating of the blood slipping agent, and explanation thereof will therefore be omitted.

[Blood Slipping Agent-Containing Composition]

The blood slipping agent-containing composition contains the aforementioned blood slipping agent and at least one other component. The other component is not particularly restricted so long as it does not inhibit the function and effect of the blood slipping agent, and it may be any one commonly employed in absorbent articles of the field, and especially top sheets.

Examples for the other component(s) include silicone oils, silicones, silicone-based resins and the like.

Examples for the other component(s) also include antioxidants, such as BHT (2,6-di-t-butyl-p-cresol), BHA (butylated hydroxyanisole) and propyl gallate.

Further examples for the other component(s) include vitamins, such as natural vitamins and synthetic vitamins. Examples of vitamins include water-soluble vitamins, such as group B vitamins, including $B_1$, vitamin $B_2$, vitamin $B_3$, vitamin $B_5$, vitamin $B_6$, vitamin $B_7$, vitamin $B_9$ and vitamin $B_{12}$, and vitamin C.

Other examples of vitamins include fat-soluble vitamins, such as group A vitamins, group D vitamins, group E vitamins and group K vitamins. Derivatives of these vitamins are also included.

Examples for the other component(s) include amino acids, such as alanine, arginine, lysine, histidine, proline and hydroxyproline, and peptides.

Other examples for the other component(s) include zeolite, such as natural zeolite, examples of which include analcite, chabazite, heulandite, natrolite, stilbite and thomosonite, and synthetic zeolite.

Still other examples for the other component(s) include cholesterol, hyaluronic acid, lecithin and ceramide.

Yet other examples for the other component(s) include drugs, such as skin astringents, anti-pimple medications, anti-wrinkle agents, anti-cellulite agents, skin whiteners, antimicrobial agents and antifungal agents.

Examples of skin astringents include zinc oxide, aluminum sulfate, tannic acid and the like, and oil-soluble skin astringents, such as fat-soluble polyphenols. Fat-soluble polyphenols include natural fat-soluble polyphenols, such as barley extract, otogiriso extract, white deadnettle extract, chamomilla extract, burdock extract, salvia extract, linden extract, common lime extract, white birch extract, common horsetail extract, sage extract, salvia extract, walnut (*J. regia* L. var. *orientalis*) extract, hibiscus extract, loquat leaf extract, Miquel's linden extract, hop extract, common horsechestnut extract and coix seed extract.

Examples of anti-pimple medications include salicylic acid, benzoyl peroxide, resorcinol, sulfur, erythromycin and zinc.

Examples of anti-wrinkle agents include lactic acid, salicylic acid, salicylic acid derivatives, glycolic acid, phytic acid, lipoic acid and lysophosphatidic acid.

Examples of anti-cellulite agents include xanthine compounds, such as aminophylline, caffeine, theophylline and theobromine.

Examples of skin whiteners include niacinamide, kojic acid, arbutin, glucosamine and its derivatives, phytosterol derivatives, and ascorbic acid and its derivatives, as well as mulberry extract and placenta extract.

Examples for the other component(s) also include anti-inflammatory components, pH regulators, antimicrobial agents, humectants, aromatics, pigments, dyes, pigments and plant extracts.

Examples of anti-inflammatory components include naturally-derived anti-inflammatory drugs, such as peony, golden grass, otogiriso, chamomile, licorice, peach leaf, Japanese mugwort and perilla extract, and synthetic anti-inflammatory drugs, such as allantoin and dipotassium glycyrrhizinate.

Examples of pH regulators include those that keep the skin weakly acidic, such as malic acid, succinic acid, citric acid, tartaric acid and lactic acid.

Titanium oxide is an example of a pigment.

The blood slipping agent-containing composition contains the blood slipping agent and the one or more other components at preferably about 50 to about 99 mass % and about 1 to about 50 mass %, respectively, more preferably about 60 to about 99 mass % and about 1 to about 40 mass %, respectively, even more preferably about 70 to about 99 mass % and about 1 to about 30 mass %, respectively, yet more preferably about 80 to about 99 mass % and about 1 to about 20 mass %, respectively, even yet more preferably about 90 to 99 mass % and about 1 to about 10 mass %, respectively, and even yet more preferably about 95 to 99 mass % and about 1 to about 5 mass %, respectively. This is from the viewpoint of the functions and effects of the blood slipping agent and the other components.

The blood slipping agent-containing composition preferably contains a surfactant in not greater than the amount from hydrophilicizing treatment of the top sheet or second sheet. More specifically, the blood slipping agent-containing composition contains a surfactant in a basis weight range of preferably about 0.0 to about 1.0 $g/m^2$, more preferably about 0.0 to about 0.8 $g/m^2$, even more preferably about 0.1 to about 0.5 $g/m^2$, and yet more preferably about 0.1 to about 0.3 $g/m^2$.

This is because when the amount of surfactant is increased, menstrual blood will tend to be retained in the top sheet. The surfactant, incidentally, has no water holding percentage. This is because there is no layer of the substance to be measured due to its mixture with water.

The blood slipping agent-containing composition contains water in a basis weight range of preferably about 0.0 to about 1.0 $g/m^2$, more preferably about 0.0 to about 0.8 $g/m^2$, even more preferably about 0.1 to about 0.5 $g/m^2$, and yet more preferably about 0.1 to about 0.3 $g/m^2$. Since water lowers the absorption performance of the absorbent article, the amount is preferably low.

Similar to the blood slipping agent, the blood slipping agent-containing composition, as a composition, has at 40° C., a kinematic viscosity of preferably about 0 to about 80 $mm^2/s$, more preferably a kinematic viscosity of about 1 to about 70 $mm^2/s$, even more preferably a kinematic viscosity of about 3 to about 60 $mm^2/s$, yet more preferably a kinematic viscosity of about 5 to about 50 $mm^2/s$, and even yet more preferably a kinematic viscosity of about 7 to about 45 $mm^2/s$.

If the kinematic viscosity of the blood slipping agent-containing composition exceeds 80 $mm^2/s$, the viscosity will increase and the blood slipping agent composition may not slide down into the interior of the absorbent article as easily with menstrual blood that has reached the skin contact surface of the top sheet.

When the blood slipping agent-containing composition contains a component that is miscible with the blood slipping agent, as at least one other component, the other component preferably has a weight-average molecular weight of less than about 1,000, and more preferably a weight-average molecular weight of less than about 900. This is because, if the weight-average molecular weight is about 1,000 or higher, tack may be produced in the blood slipping agent-containing composition itself, tending to create a feeling of discomfort for the wearer. If the weight-average molecular weight increases, the viscosity of the blood slipping agent-containing composition will tend to increase, and it will therefore be difficult to lower the viscosity of the blood slipping agent composition by heating to a viscosity suitable for coating, and as a result, the blood slipping agent may need to be diluted with a solvent.

The blood slipping agent-containing composition, as a composition, has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

A low water holding percentage value will tend to lower the affinity between the blood slipping agent composition and menstrual blood, thus inhibiting it from sliding down into the interior of the absorbent article with menstrual blood that has reached the skin contact surface of the top sheet.

When the blood slipping agent-containing composition contains solid matter, it is preferably removed by filtration for measurement of the kinematic viscosity and water holding percentage.

EXAMPLES

Test Example 1

The blood slipping agents used for the test examples are listed below.
[($a_1$) Ester of a Chain Hydrocarbon Tetraol and at Least One Fatty Acid]
UNISTAR H-408BRS, product of NOF Corp.
Pentaerythritol tetra(2-ethylhexanoate), weight-average molecular weight: approximately 640
UNISTAR H-2408BRS-22, product of NOF Corp.
Mixture of pentaerythritol tetra(2-ethylhexanoate) and neopentylglycol di(2-ethylhexanoate) (58:42 as weight ratio), weight-average molecular weight: approximately 520
[($a_2$) Ester of a Chain Hydrocarbon Triol and at Least One Fatty Acid]
Cetiol SB45DEO, Cognis Japan
Glycerin and fatty acid triester, with oleic acid or stearylic acid as the fatty acid.
SOY42, product of NOF Corp.
Glycerin and fatty acid triester with $C_{14}$ fatty acid:$C_{16}$ fatty acid: $C_{18}$ fatty acid:$C_{20}$ fatty acid (including both saturated fatty acids and unsaturated fatty acids) at a mass ratio of about 0.2:11:88:0.8, weight-average molecular weight: 880
Tri-C2L oil fatty acid glyceride, product of NOF Corp.
Glycerin and fatty acid triester with $C_8$ fatty acid:$C_{10}$ fatty acid:$C_{12}$ fatty acid at a weight ratio of about 37:7:56, weight-average molecular weight: approximately 570
Tri-CL oil fatty acid glyceride, product of NOF Corp.
Glycerin and fatty acid triester with $C_8$ fatty acid:$C_{12}$ fatty acid at a weight ratio of about 44:56, weight-average molecular weight: approximately 570
PANACET 810s, product of NOF Corp.
Glycerin and fatty acid triester with $C_8$ fatty acid:$C_{10}$ fatty acid at a weight ratio of about 85:15, weight-average molecular weight: approximately 480
PANACET 800, product of NOF Corp.
Glycerin and fatty acid triester with octanoic acid ($C_8$) as the entire fatty acid portion, weight-average molecular weight: approximately 470.
PANACET 800B, product of NOF Corp.
Glycerin and fatty acid triester with 2-ethylhexanoic acid ($C_8$) as the entire fatty acid portion, weight-average molecular weight: approximately 470
NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a weight ratio of about 5:92:3, weight-average molecular weight: approximately 880
Tri-coconut fatty acid glyceride, product of NOF Corp.
Glycerin and fatty acid triester with $C_8$ fatty acid: $C_{10}$ fatty acid:$C_{12}$ fatty acid:$C_{14}$ fatty acid:$C_{16}$ fatty acid (including both saturated fatty acids and unsaturated fatty acids) at a weight ratio of about 4:8:60:25:3, weight-average molecular weight: 670
Caprylic acid diglyceride, product of NOF Corp.
Glycerin and fatty acid diester with octanoic acid as the fatty acid, weight-average molecular weight: approximately 340
[($a_3$) Ester of a Chain Hydrocarbon Diol and at Least One Fatty Acid]
UNISTAR H-208BRS, product of NOF Corp.
Neopentyl glycol di(2-ethylhexanoate), weight-average molecular weight: approximately 360
COMPOL BL, product of NOF Corp.
Dodecanoic acid ($C_{12}$) monoester of butylene glycol, weight-average molecular weight: approximately 270
COMPOL BS, product of NOF Corp.
Octadecanoic acid ($C_{18}$) monoester of butylene glycol, weight-average molecular weight: approximately 350
[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]
Tributyl O-acetylcitrate, product of Tokyo Kasei Kogyo Co., Ltd.
Weight-average molecular weight: approximately 400
Tributyl citrate, product of Tokyo Kasei Kogyo Co., Ltd.
Weight-average molecular weight: approximately 360
[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]
Dioctyl adipate, product of Wako Pure Chemical Industries, Ltd.
Weight-average molecular weight: approximately 380
[($d_3$) Esters of a Fatty Acid and Aliphatic Monohydric Alcohol]
ELECTOL WE20, product of NOF Corp.
Ester of dodecanoic acid ($C_{12}$) and dodecyl alcohol ($C_{12}$), weight-average molecular weight: approximately 360
ELECTOL WE40, product of NOF Corp.

Ester of tetradecanoic acid ($C_{14}$) and dodecyl alcohol ($C_{12}$), weight-average molecular weight: approximately 390

[($e_1$) Polyoxy $C_3$-$C_6$ Alkylene Glycol]

UNIOL PB500, product of NOF Corp.
Polybutylene glycol, weight-average molecular weight: approximately 500
UNIOL PB700, product of NOF Corp.
Polyoxybutylene polyoxypropylene glycol, weight-average molecular weight: approximately 700

[($f_1$) Chain Alkane]

PARLEAM 6, product of NOF Corp.
Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.
Glycerin and fatty acid triester obtained by addition of hydrogen to NA36 for reduced proportion of double bonds from unsaturated fatty acid starting material, weight-average molecular weight: approximately 880
(Caprylic acid/capric acid) monoglyceride, product of NOF Corp.
Glycerin and fatty acid monoester, with octanoic acid ($C_8$) and decanoic acid ($C_{10}$) at a weight ratio of about 85:15, weight-average molecular weight: approximately 220
Monomuls 90-L2 lauric acid monoglyceride, product of Cognis Japan
Isopropyl citrate, product of Tokyo Kasei Kogyo Co., Ltd.
Weight-average molecular weight: approximately 230
Diisostearyl malate
Weight-average molecular weight: approximately 640
UNIOL PB1000R, product of NOF Corp.
Polybutylene glycol, weight-average molecular weight: approximately 1,000
UNIOL D-250, product of NOF Corp.
Polypropylene glycol, weight-average molecular weight: approximately 250
UNIOL D-400, product of NOF Corp.
Polypropylene glycol, weight-average molecular weight: approximately 400
UNIOL D-700, product of NOF Corp.
Polypropylene glycol, weight-average molecular weight: approximately 700
UNIOL D-1000, product of NOF Corp.
Polypropylene glycol, weight-average molecular weight: approximately 1,000
UNIOL D-1200, product of NOF Corp.
Polypropylene glycol, weight-average molecular weight: approximately 1,160
UNIOL D-2000, product of NOF Corp.
Polypropylene glycol, weight-average molecular weight: approximately 2,030
UNIOL D-3000, product of NOF Corp.
Polypropylene glycol, weight-average molecular weight: approximately 3,000
UNIOL D-4000, product of NOF Corp.
Polypropylene glycol, weight-average molecular weight: approximately 4,000
PEG1500, product of NOF Corp.
Polyethylene glycol, weight-average molecular weight: approximately 1,500-1,600
WILBRITE cp9, product of NOF Corp.
Polybutylene glycol compound with OH groups at both ends esterified by hexadecanoic acid ($C_{16}$), weight-average molecular weight: approximately 1,150
UNILUBE MS-70K, product of NOF Corp.
Stearyl ether of polypropylene glycol, approximately 15 repeating units, weight-average molecular weight: approximately 1,140
NONION S-6, product of NOF Corp.
Polyoxyethylene monostearate, approximately 7 repeating units, weight-average molecular weight: approximately 880
UNILUBE 5TP-300 KB
Polyoxyethylenepolyoxypropylene pentaerythritol ether, produced by addition of 5 mol of ethylene oxide and 65 mol of propylene oxide to 1 mol of pentaerythritol, weight-average molecular weight: 4,130
WILBRITE s753, product of NOF Corp.
Polyoxyethylene polyoxypropylene polyoxybutylene glycerin, weight-average molecular weight: approximately 960
UNIOL TG-330, product of NOF Corp.
Glyceryl ether of polypropylene glycol, approximately 6 repeating units, weight-average molecular weight: approximately 330
UNIOL TG-1000, product of NOF Corp.
Glyceryl ether of polypropylene glycol, approximately 16 repeating units, weight-average molecular weight: approximately 1,000
UNIOL TG-3000, product of NOF Corp.
Glyceryl ether of polypropylene glycol, approximately 16 repeating units, weight-average molecular weight: approximately 3,000
UNIOL TG-4000, product of NOF Corp.
Glyceryl ether of polypropylene glycol, approximately 16 repeating units, weight-average molecular weight: approximately 4,000
UNILUBE DGP-700, product of NOF Corp.
Diglyceryl ether of polypropylene glycol, approximately 9 repeating units, weight-average molecular weight: approximately 700
UNIOX HC60, product of NOF Corp.
Polyoxyethylene hydrogenated castor oil, weight-average molecular weight: approximately 3,570
Vaseline, product of Cognis Japan
Petroleum-derived hydrocarbon, semi-solid Test Example 2

Menstrual Blood Surface Residue Rate a, with Absorption of Large Amount of Blood A test was conducted to evaluate the absorption property of a sanitary napkin after one-time absorption of a large amount of blood.

There were prepared a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic superabsorbent polymer (basis weight: 15 g/m$^2$) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, with the pitch of the ridge-furrow structure (ridge width furrow width) at approximately 4 mm and open holes formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 1-1.

Sanitary napkins No. 1-2 to No. 1-49 were produced, changing the blood slipping agent from UNISTAR H-408BRS to the ones listed in Table 2. Each blood slipping agent was used directly, when it was liquid at room temperature, or when the blood slipping agent was solid at room temperature it was heated to its melting point +20° C., and then a control seam HMA gun was used for atomization of the blood slipping agent and coating onto the skin contact surface of the top sheet to a basis weight of about 5 g/m².

The blood slipping agent was coated onto essentially the entire skin contact surface of the top sheet, and on both the ridges and furrows.

[Test Methods]

After measuring the mass $W_2$ (g) of the top sheet (the weight of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the mass $W_3$ (g) (mass of the top sheet after the test) was measured and the "surface residue rate A (mass %)" was calculated by the following formula.

Surface residue rate $A$ (mass %)=100×[$W_3$ (g)−$W_2$ (g)]/4.0 (g)

The tack on the skin contact surface of the top sheet was measured at 35° C., and evaluated on the following scale.
G: No tack
F: Slight tack
P: Tack The surface residue rate A and tack of each absorbent article, and the properties of each blood slipping agent, are shown below in Table 2. FIG. 6 is an electron micrograph of the skin contact surface of a top sheet in a sanitary napkin wherein the top sheet comprises tri-C2L oil fatty acid glycerides.

TABLE 2

| No. | Blood slipping agent | Kinematic viscosity (mm²/s, 40° C.) | Water holding percentage (mass %) | Weight-average molecular weight | IOB | Melting point (° C.) | Surface residue rate A (mass %) | Tack |
|---|---|---|---|---|---|---|---|---|
| 1-1 | H-408 BRS | 45 | 0.7 | 640 | 0.13 | <−5 | 0.8 | G |
| 1-2 | H-2408 BRS-22 | 22 | 0.8 | 520 | 0.18 | <−5 | 0.8 | G |
| 1-3 | Tri-C2L oil fatty acid glyceride | 20 | <1.0 | 570 | 0.27 | 37 | | G |
| 1-4 | Tri-CL oil fatty acid glyceride | 15 | <1.0 | 570 | 0.28 | 38 | | G |
| 1-5 | PANACET 810s | 9 | 0.3 | 480 | 0.32 | −5 | 0.8 | G |
| 1-6 | PANACET 800 | 15 | 0.5 | 470 | 0.33 | −5 | 1.8 | G |
| 1-7 | PANACET 800B | 20 | <1.0 | 470 | 0.33 | −5 | | G |
| 1-8 | NA36 | 40 | <1.0 | 880 | 0.16 | 37 | | G |
| 1-9 | Tri-coconut oil fatty acid glyceride | 25 | <1.0 | 670 | 0.28 | 30 | | G |
| 1-10 | Caprylic acid diglyceride | 25 | 2.7 | 340 | 0.58 | <45 | 1.0 | G |
| 1-11 | UNISTAR H-208BRS | 8 | 0.7 | 360 | 0.24 | <−5 | 0.5 | G |
| 1-12 | COMPOL BL | 10 | 1.6 | 270 | 0.50 | 2 | 1.3 | G |
| 1-13 | COMPOL BS | 35 | 0.3 | 350 | 0.36 | 37 | 2.5 | G |
| 1-14 | Tributyl O-acetylcitrate | 15 | 0.9 | 400 | 0.60 | <45 | 0.5 | G |
| 1-15 | Tributyl citrate | 12 | 0.6 | 360 | 0.78 | <45 | 1.8 | G |
| 1-16 | Dioctyl adipate | 7 | 0.4 | 380 | 0.27 | <45 | 1.5 | G |
| 1-17 | ELECTOL WE20 | 10 | 0.3 | 360 | 0.13 | 29 | 0.5 | G |
| 1-18 | ELECTOL WE40 | 15 | 0.5 | 390 | 0.12 | 37 | 2.3 | G |
| 1-19 | UNIOL PB500 | 40 | 3.6 | 500 | 0.44 | <45 | 2.5 | G |
| 1-20 | UNIOL PB700 | 50 | 2.3 | 700 | 0.49 | −5 | 1.3 | G |
| 1-21 | PARLEAM 6 | 5 | 0.06 | 330 | 0.00 | −5 | 2.0 | G |
| 1-22 | NA50 | 80<< | —* | 880 | 0.18 | 52 | 4.3 | G |
| 1-23 | (Caprylic acid/capric acid) monoglyceride | 70 | 4.0<< | 220 | 1.15 | <45 | 5.0 | G |
| 1-24 | 90-L2 lauric acid monoglyceride | 80<< | 4.0<< | <1,000 | 0.87 | 58 | 5.0 | G |
| 1-25 | Isopropyl citrate | 120 | 4.0<< | 230 | 1.56 | <45 | 4.8 | F |
| 1-26 | Diisostearyl malate | 450 | 4.0<< | 640 | 0.28 | <45 | 3.3 | F |
| 1-27 | UNIOL PB1000R | 70 | 5.5 | 1000 | 0.40 | <45 | 2.5 | F |
| 1-28 | UNIOL D-250 | 20 | 4.0<< | 250 | | <45 | 3.8 | G |
| 1-29 | UNIOL D-400 | 30 | 4.0<< | 400 | 0.76 | <45 | 4.8 | G |
| 1-30 | UNIOL D-700 | 50 | 34.6 | 700 | 0.58 | <45 | 4.8 | G |
| 1-31 | UNIOL D-1000 | 70 | 26.7 | 1,000 | 0.51 | <45 | 3.8 | F |
| 1-32 | UNIOL D-1200 | 90 | 16.2 | 1,160 | 0.48 | <45 | 3.0 | F |
| 1-33 | UNIOL D-2000 | 160 | | 2,030 | | <45 | | P |
| 1-34 | UNIOL D-3000 | | 0.6 | 3,000 | 0.39 | <45 | 3.0 | P |
| 1-35 | UNIOL D-4000 | 450 | 0.5 | 4,000 | 0.38 | <45 | 2.5 | P |
| 1-36 | PEG 1500 | 120 | 4.0<< | 1,500-1,600 | 0.78 | 40 | 5.5 | P |
| 1-37 | WILBRITE CP9 | 120 | 0.6 | 1,150 | 0.21 | 35 | 6.8 | P |
| 1-38 | UNILUBE MS-70K | 50 | 2.8 | 1,140 | 0.30 | <−10 | 1.5 | F |

TABLE 2-continued

| No. | Blood slipping agent | Kinematic viscosity (mm²/s, 40° C.) | Water holding percentage (mass %) | Weight-average molecular weight | IOB | Melting point (° C.) | Surface residue rate A (mass %) | Tack |
|---|---|---|---|---|---|---|---|---|
| 1-39 | NONION S-6 | 65 | 4.0<< | 880 | 0.44 | 37 | | G |
| 1-40 | UNILUBE 5TP-300KB | 310 | 3.9 | 4,130 | 0.39 | <45 | 2.0 | P |
| 1-41 | WILBRITE s753 | 120 | 27.3 | 960 | 0.67 | −5 | 3.5 | F |
| 1-42 | UNIOL TG-330 | 30 | | 330 | 1.27 | <45 | | G |
| 1-43 | UNIOL TG-1000 | 100 | 21.2 | 1,000 | 0.61 | <45 | 3.5 | G |
| 1-44 | UNIOL TG-3000 | 230 | 4.3 | 3,000 | 0.42 | <45 | 1.0 | P |
| 1-45 | UNIOL TG-4000 | 300 | 2.4 | 4,000 | 0.40 | <45 | 2.0 | P |
| 1-46 | UNILUBE DGP-700 | 200 | 4.0<< | 700 | 0.91 | <0 | 3.5 | F |
| 1-47 | UNIOX HC60 | 1150 | | 3,570 | 0.46 | 33 | | P |
| 1-48 | Vaseline | 80<< | 0.0 | <1,000 | 0.00 | 55 | 4.0 | P |
| 1-49 | None | — | — | — | — | — | 7.5 | G |

*High viscosity, unmeasurable.

With sanitary napkin No. 1-49, which had no blood slipping agent, the surface residue rate A was 7.5 mass %, but with sanitary napkins No. 1-1 to No. 1-21 wherein the kinematic viscosity and water holding percentage were within the prescribed ranges, the surface residue rate A was 2.5 mass % or lower.

With sanitary napkins No. 1-1 to No. 1-21, it was observed that the horse EDTA blood that was dropped onto the ridges of the top sheet slid down from the ridges into the furrows, and was rapidly absorbed from the furrows into the absorbent body. However, with sanitary napkin No. 1-49 which had no blood slipping agent, the dropped horse EDTA blood did not slip down into the furrows but slowly dripped down into the furrows, most of it remaining on the ridges of the top sheet. Also, with the absorbent articles with high a water holding percentage, as with No. 1-30, for example, the horse EDTA blood that was dropped onto the ridges of the top sheet did not slip down into the furrows but slowly dripped while partially remaining on the top sheet, and a portion thereof remained on the ridges.

This suggests that sanitary napkins No. 1-1 to No. 1-21 allow rapid migration of menstrual blood from the top sheet into the absorbent body, when a large amount of menstrual blood has reached the top sheet at once.

Next, several volunteer subjects were asked to wear sanitary napkins Nos. 1-1 to 1-49, and most of the obtained responses indicated that with the sanitary napkins comprising blood slipping agents Nos. 1-1 to 1-21, the top sheets had no sticky feel and the top sheets were smooth, even after absorption of menstrual blood.

For this test example there was used a top sheet having a ridge-furrow structure produced by the method described in Japanese Unexamined Patent Publication No. 2008-2034, but the blood slipping agent exhibits the same blood slipping effect when using a top sheet having a ridge-furrow structure produced by a different method, or when using a top sheet having an irregular structure other than a ridge-furrow structure, and can presumably cause menstrual blood to rapidly migrate from the top sheet into the absorbent body (see Test Example 8).

Test Example 3

Menstrual Blood Surface Residue Rate B, with Absorption of Small Amount of Blood A test was conducted to evaluate the absorption property of a sanitary napkin after absorption of a small amount of blood.

There were prepared a top sheet, formed of a hydrophilic agent-treated air-through nonwoven fabric (composite fiber composed of polyester and polyethylene terephthalate, basis weight: 35 g/m²) (hereunder also referred to as "top sheet with ridge-furrows"), a second sheet formed of an air-through nonwoven fabric (composite fibers composed of polyester and polyethylene terephthalate, basis weight: 30 g/m²), an absorbent body comprising pulp (basis weight: 150 to 450 g/m², increased at the center section), an acrylic super-absorbent polymer (basis weight: 15 g/m²) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, and the pitch of the ridge-furrow structure (ridge width+furrow width) was approximately 4 mm and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 2-1(i).

A sanitary napkin No. 2-1(ii) was formed in the same manner as the sanitary napkin No. 2-1(i), except that the top sheet was changed to a top sheet formed of a flat hydrophilic agent-treated air-through nonwoven fabric (composite fiber composed of polyester and polyethylene terephthalate, basis weight: 35 g/m²), without a ridge-furrow structure (hereunder also referred to as "flat top sheet").

Sanitary napkins No. 2-2(i) to No. 2-11(i) and No. 2-2(ii) to No. 2-11(ii) were produced, changing the blood slipping agent from UNISTAR H-408BRS to the ones listed in Table 3. Each blood slipping agent was used directly, when it was liquid at room temperature, or when the blood slipping agent was solid at room temperature it was heated to its melting point +20° C., and then a control seam HMA gun was used for atomization of the blood slipping agent and coating onto the skin contact surface of the top sheet to a basis weight of about 5 g/m².

The blood slipping agent was coated over essentially the entire skin contact surface of the top sheet, and on both the ridges and furrows of the top sheets with a ridge-furrow structure.

[Test Methods]

After measuring the mass $W_4$ (g) of the top sheet (the weight of the top sheet before the test), approximately 0.25 g (2 drops) of horse EDTA blood at 37±1° C. was added dropwise through a pipette, on the top sheet at the center in the lengthwise direction and widthwise direction of the absorbent article. The horse EDTA blood was dropped onto the top parts of the ridges, in the top sheets with ridge-furrows.

At 30 seconds after dropping, the top sheet was taken off, the mass $W_5$ (g) (mass of top sheet after the test) was measured and the "surface residue rate B (mass %)" was calculated by the following formula.

Surface residue rate $B$ (mass %)=100×($W_5$ (g)−$W_4$ (g))/$W_6$ (g)

$W_6$ (g) is the mass of the dropped horse EDTA blood, calculated from the weight of the pipette before and after dropping.

The results are shown in Table 3 below.

TABLE 3

| No. | Blood slipping agent | Surface residue rate B (mass %) | |
|---|---|---|---|
| | | Top sheet with ridge-furrows | Flat top sheet |
| 2-1 | H-408 BRS | 4% | 32% |
| 2-2 | PANACET 810S | 8% | 40% |
| 2-3 | Capric acid diglyceride | 8% | 24% |
| 2-4 | COMPOL BL | 4% | 32% |
| 2-5 | Tributyl O-acetylcitrate | 8% | 44% |
| 2-6 | Dioctyl adipate | 8% | 32% |
| 2-7 | ELECTOL WE40 | 8% | 24% |
| 2-8 | UNIOL PB500 | 4% | 68% |
| 2-9 | PARLEAM 6 | 4% | 100% |
| 2-10 | UNIOL D-250 | 16% | 48% |
| 2-11 | None | 28% | 28% |

Table 3 shows that when the blood slipping agent was H-408BRS, PANACET 810S, capric acid diglyceride, COMPOL BL, tributyl O-acetylcitrate, dioctyl adipate, ELECTOL WE40, UNIOL PB500 or PARLEAM 6, the surface residue rate B of the top sheet with ridge-furrows was low. This suggests that blood slipping agents having the prescribed properties cause rapid migration of small amounts of blood from the ridges to the furrows and into the absorbent body.

For this test example there was used a top sheet having a ridge-furrow structure produced by the method described in Japanese Unexamined Patent Publication No. 2008-2034, but the blood slipping agent exhibits the same blood slipping effect when using a top sheet having a ridge-furrow structure produced by a different method, or when using a top sheet having an irregular structure other than a ridge-furrow structure, and can presumably cause menstrual blood to rapidly migrate from the top sheet into the absorbent body (see Test Example 8).

Test Example 4

Viscosity of Blood Containing Blood Slipping Agent

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate, due to the parallel plate, but the average shear rate indicated by the device was $10\ s^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and it is believed that the blood slipping agent of the present disclosure has an effect of lowering the viscosity of blood, such as menstrual blood in the low viscosity range. Lowering the blood viscosity presumably allows absorbed menstrual blood to more easily migrate rapidly from the top sheet to the absorbent body.

Test Example 5

Photomicrograph of Blood Slipping Agent-Containing Blood

Menstrual blood was sampled from healthy volunteers onto food storage wrap film, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 7(a), and a photomicrograph of menstrual blood containing PANACET 810s is shown in FIG. 7(b).

Figure 7:
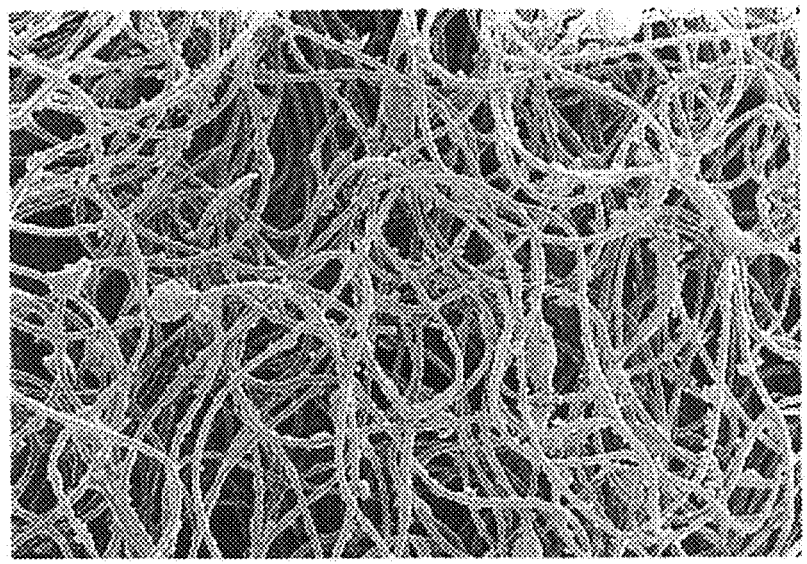
FIG. 7 is an electron micrograph of the skin contact surface of a top sheet in a sanitary napkin wherein the top sheet comprises tri-C2L oil fatty acid glycerides.

As shown in FIG. 7, the erythrocytes formed aggregates, including a rouleaux structure, in the menstrual blood containing no blood slipping agent, while the erythrocytes were stably dispersed in the menstrual blood containing PANACET 810s. This suggests that the blood slipping agent has the function of stabilizing erythrocytes in blood.

Test Example 6

Surface Tension of Blood Containing Blood Slipping Agent

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

Figure 8:
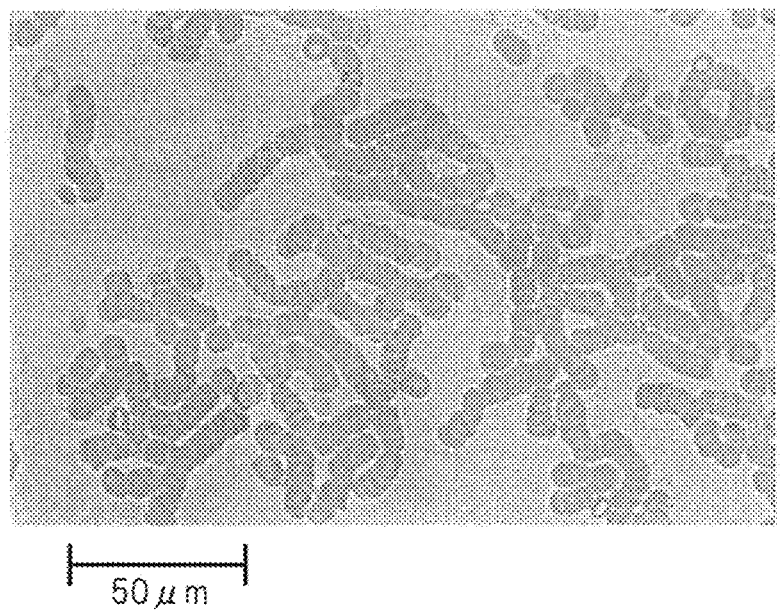
FIG. 8 is a pair of photomicrographs of menstrual blood containing and not containing a blood slipping agent.
Figure 8:
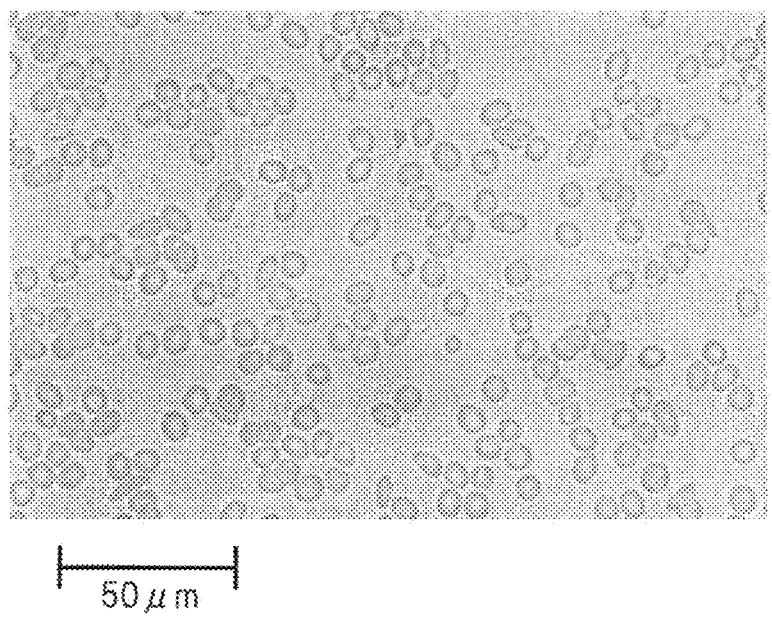

The measurement was accomplished automatically with the apparatus, and the surface tension 7 was determined by the following formula (see FIG. 8).

$\gamma = g \times \rho \times (de)^2 \times 1/H$ g: Gravitational constant
1/H: Correction factor determined from ds/de
ρ: Density
de: Maximum diameter ds: Diameter at location of increase by de from dropping edge The density ρ was measured at the temperatures listed in Table 4, according to JIS K 2249-1995, "Density test methods and density/mass/volume conversion tables", 5. Vibrating density test method.

The measurement was accomplished using a DA-505 by Kyoto Electronics Co., Ltd.

The results are shown in Table 4 below.

TABLE 4

| No. | Blood slipping agent | | Measuring temperature (° C.) | Surface tension (mN/m) |
|---|---|---|---|---|
| | Type | Amount (mass %) | | |
| 1 | — | — | 35 | 62.1 |
| 2 | PANACET 810s | 0.01 | 35 | 61.5 |
| 3 | | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Based on Table 4 it is seen that the blood slipping agent has an effect of lowering the surface tension of blood.

Lowering the surface tension of blood presumably allows absorbed blood to rapidly migrate from the top sheet to the absorbent body, without being retained between the top sheet fibers.

Test Example 7

(1) Preparation of Samples A1-C1 and A2-C2

Three different commercially available sanitary napkins A-C were prepared.

Sanitary napkin A (Sofy Hadaomoi by Unicharm Corp.) has a top sheet with an irregular structure formed on the skin contact surface (air-through nonwoven fabric composed of PET/HDPE core-sheath composite fibers, basis weight: 35 g/m$^2$) as a liquid-permeable layer, and a second sheet situated between the top sheet and the absorbent body (air-through nonwoven fabric composed of PET/HDPE core-sheath composite fibers, basis weight: 38 g/m$^2$). The irregular structure formed on the skin contact surface of the top sheet was a ridge-furrow structure formed by the method described in Japanese Unexamined Patent Publication No. 2008-2034, the thickness of the ridges being approximately 1.5 mm, the thickness of the furrows being approximately 0.4 mm, the pitch of the ridge-furrow structure (ridge width furrow width) being approximately 4 mm and the open area of the open holes formed in the furrows being approximately 15%.

The sanitary napkin B used was "Laurier F" by Kao Corp. Sanitary napkin 1 had a top sheet with an irregular structure formed on the skin contact surface, as a liquid-permeable layer.

The sanitary napkin C used was "Laurier Speed Plus" by Kao Corp. Sanitary napkin C had a top sheet with an irregular structure formed on the skin contact surface, as a liquid-permeable layer.

The skin contact surfaces of sanitary napkins A to C were coated with a blood slipping agent (triglyceride) to produce samples A1 to C1. Separately, sanitary napkins A to C, not coated with a blood slipping agent, were prepared as samples A2 to C2. The coating basis weight of the blood slipping agent was 10 g/m$^2$ for sample A1, 16 g/m$^2$ for sample B1 and 57.6 g/m$^2$ for sample C1.

(2) Measurement of Rewetting Amount and Absorbent Body Migration Rate

[Test Methods]

An acrylic board with an opened hole (200 mm×100 mm, 125 g, with a 40 mm×10 mm hole opened at the center) was placed on the skin contact surface of each sample, and 3 mL of horse EDTA blood at 37±1° C. (obtained by adding ethylenediaminetetraacetic acid (EDTA) to horse blood to prevent coagulation) was dropped through the hole using a pipette (first time), and after 1 minute, 3 mL of horse EDTA blood at 37±1° C. was again added dropwise through the acrylic board hole with a pipette (second time). The dropping rate was 90 mL/min.

After the second dropping of blood, the acrylic board was immediately removed and filter paper (Qualitative filter paper No. 2, product of Advantech Toyo, Inc., 50 mm×35 mm) was placed on the location where the blood had been dropped, and then a weight was placed thereover to a pressure of 30 g/cm$^2$. After 1 minute, the filter paper was removed and the rewetting amount (weight of filter paper after test−weight of filter paper before test) was calculated.

Separately from evaluation of the rewetting amount, the migration time of blood from the liquid-permeable layer into the absorbent body after the second dropping of the blood was measured, and was recorded as the absorbent body migration rate (drain time). The absorbent body migration rate is the time from introduction of blood into the liquid-permeable layer until the redness of the blood is no longer visible on the surface and interior of the liquid-permeable layer.

[Results]

The rewetting amount of sample A1 was 0.05 g and the absorbent body migration rate was 8 seconds, while the rewetting amount of sample A2 was 1.06 g and the absorbent body migration rate was longer than 60 seconds.

The rewetting amount of sample B1 was 0.92 g and the absorbent body migration rate was 27 seconds, while the rewetting amount of sample B2 was 1.47 g and the absorbent body migration rate was longer than 60 seconds.

The rewetting amount of sample C1 was 0.61 g and the absorbent body migration rate was 28 seconds, while the rewetting amount of sample C2 was 0.60 g and the absorbent body migration rate was longer than 60 seconds.

With sample A1, the rewetting amount was notably reduced compared to sample A2, and the absorbent body migration rate was notably increased. This suggests that the function and effect of the blood slipping agent were effectively exhibited with sample 1A.

In contrast, the rewetting amount was reduced and the absorbent body migration rate was increased with sample B1 compared to sample B2, although the amount of increase in the absorbent body migration rate was not as notable as with sample A1. This suggests that the function and effect of the blood slipping agent were not as effectively exhibited with sample B1 compared to sample A1.

Also, the absorbent body migration rate was increased with sample C1 compared to sample C2, although the amount of increase in the absorbent body migration rate was not as notable as with sample A1. The rewetting amount was unchanged with sample C1 compared to sample C2. This suggests that the function and effect of the blood slipping agent were not as effectively exhibited with sample C1 compared to sample A1.

The cause of the lack of an effective function and effect of the blood slipping agent with samples B1 and C1 was therefore examined.

With sample A1, in the liquid-permeable layer, the basis weight was 35 g/m² and the thickness was 0.8 mm on the upper layer (top sheet) while the basis weight was 38 g/m² and the thickness was 0.7 mm on the lower layer (second sheet), and the density of the upper layer was 0.04 g/cm³ while the density of the lower layer was 0.06 g/cm³.

In contrast, in the liquid-permeable layer of sample B1, the basis weight was 30 g/m² and the thickness was 0.9 mm on the upper layer while the basis weight was 38 g/m² and the thickness was 0.3 mm on the lower layer, and the density of the upper layer was 0.03 g/cm³ while the density of the lower layer was 0.15 g/cm³.

Also, in the liquid-permeable layer of sample C1, the basis weight was 24.5 g/m² and the thickness was 0.5 mm on the upper layer while the basis weight was 30 g/m² and the thickness was 0.3 mm on the lower layer, and the density of the upper layer was 0.05 g/cm³ while the density of the lower layer was 0.12 g/cm³.

The densities of the upper layers were not significantly different between samples A1 to C1, but the densities of the lower layers were significantly increased in samples B1 and C1 compared to sample A1. This suggests that the function and effect of the blood slipping agent are affected by the densities of the upper layer and the lower layer. Specifically, it suggests that if the density of the lower layer is greater than the density of the upper layer, the density of the lower layer being 0.1 g/cm³ or less and the density of the upper layer being 0.05 g/cm³ or less, then the function and effect of the blood slipping agent can be effectively exhibited.

Test Example 8

(1) Preparation of Samples D1 and D2

A laminated sheet was prepared having a non-heat-shrinkable fiber layer (basis weight: 15 g/m²) and a heat-shrinkable fiber layer (basis weight: 15 g/m²) for the upper layer and lower layer, respectively. The non-heat-shrinkable fiber layer was a web having a content of PET/PE core-sheath composite fibers (3.3 dtex×51 mm, 4% titanium oxide content in core) of 100 mass %, and the heat-shrinkable fiber layer (latent crimping fiber layer) was a web having a content of coPP (PP copolymer/PP side-by-side composite fibers (2.2 dtex×51 mm) of 20 mass % and a content of PET/PE core-sheath composite fibers (2.2 dtex×51 mm, 4% titanium oxide content in core) of 80 mass %. Both fibers were subjected to hydrophilicizing treatment with a surfactant.

Figure 9:
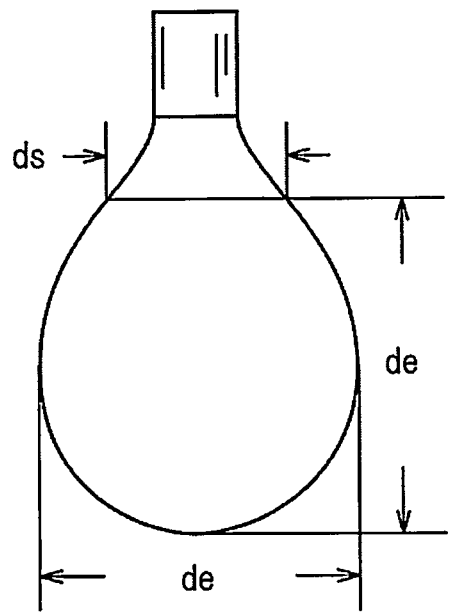
FIG. 9 is a diagram illustrating a method of measuring surface tension.
Figure 10:
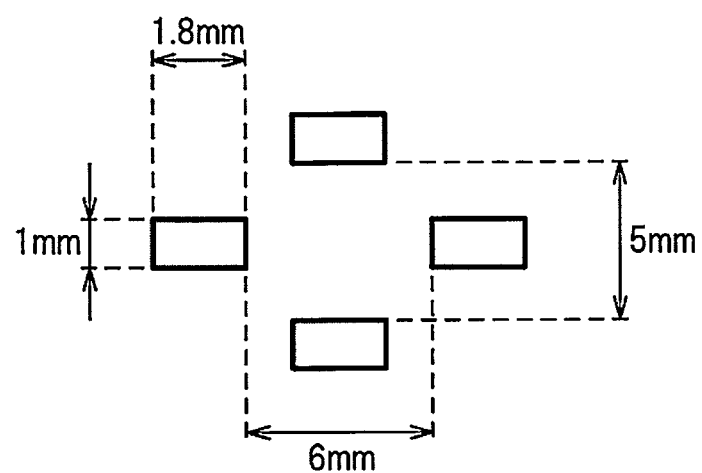
FIG. 10 is a partial enlarged plan view of the embossing roll used in Test Example 8.

The laminated sheet was subjected to heat embossing treatment from the heat-shrinkable fiber layer side, to form a heat embossed section where the non-heat-shrinkable fiber layer and heat-shrinkable fiber layer were integrated. For the heat embossing treatment there was used an embossing roll having a plurality of projections arranged in a zigzag fashion. The sizes and arranged spacing of the projections of the embossing roll were as shown in FIG. 9 (partially enlarged plan view of embossing roll), and the heights were 1 mm. The treatment temperature for the heat embossing treatment was 130° C., the treatment time was 1 second and the pressure was 15 kgf/mm².

Following heat embossing treatment, a floating dryer was used for heat treatment of the laminated sheet, producing heat stretching of the heat-extendable fiber, heat shrinkage of the heat-shrinkable fiber and heat fusion between the fibers. The treatment temperature for the heat treatment was 133° C. to 135° C., the wind speed was 5 m/sec and the line speed was 5 m/min. The area shrinkage factor of the laminated sheet after heat treatment was 50% in the MD direction and 30% in the CD direction.

Thus, a top sheet having an irregular structure formed on the skin contact surface was prepared, and the top sheet was used to produce a sanitary napkin (the absorbent body comprising pulp at a basis weight of 250 g/m², and the interface between the top sheet and the absorbent body being joined with a hot-melt adhesive at a basis weight of a 5 g/m²), coating a blood slipping agent (triglyceride) on the skin contact surface of the top sheet at a basis weight of 3 g/m². A blood slipping agent-coated article was used as sample D1, and a non-blood slipping agent-coated article was used as sample D2.

(2) Measurement of Penetration Time, Absorbent Body-Migration Time (Drain Time) and Rewetting Rate

[Test Methods]

An acrylic board with an opened hole (200 mm×100 mm, 125 g, with a 40 mm×10 mm hole opened at the center) was placed on the skin contact surface of each sample, and 3 mL of horse EDTA blood at 37±1° C. (obtained by adding ethylenediaminetetraacetic acid (EDTA) to horse blood to prevent coagulation) was dropped through the hole using a pipette (first time), and after 1 minute, 3 mL of horse EDTA blood at 37±1° C. was again added dropwise through the acrylic board hole with a pipette (second time). The dropping rate was 90 mL/min. The time from each dropping until the horse blood retained in the acrylic board hole disappeared, was recorded as the penetration time (sec), while the time until the horse blood disappeared from the surface and interior of the top sheet (the time until blood redness was no longer visible) was measured and recorded as the absorbent body migration rate (drain time) (sec).

After the second dropping of blood, the acrylic board was immediately removed and 10 sheets of filter paper (Qualitative filter paper No. 2, product of Advantech Toyo, Inc., 50 mm×35 mm) were placed on the location where the blood had been dropped, and then a weight was placed thereover to a pressure of 30 g/cm². After 1 minute, the filter paper was removed and the rewetting rate was calculated by the following formula.

Rewetting rate (%)=100×(filter paper mass after test−initial filter paper mass)/6

[Results]

With sample D1, the liquid permeation rate (1st time) was 2 seconds, the liquid permeation rate (2nd time) was 2.67 seconds, the absorbent body migration rate (1st time) was 12.42 seconds, the absorbent body migration rate (2nd time) was 27.78 seconds, and the rewetting rate was 1.2%.

In contrast, with sample D2, the liquid permeation rate (1st time) was 2.35 seconds, the liquid permeation rate (2nd time) was 2.48 seconds, the absorbent body migration rate (1st time) was 12.75 seconds, the absorbent body migration rate (2nd time) was longer than 60 seconds, and the rewetting rate was 4.3%.

This test example demonstrated that even when using a top sheet having an irregular structure formed on the skin contact surface by heat stretching of the heat-extendable fibers and/or heat shrinkage of the heat-shrinkable fibers, it is possible for the blood slipping agent to exhibit a blood-slipping function and allow menstrual blood to rapidly migrate from the top sheet into the absorbent body.

Test Example 9

(1) Preparation of Samples E1 and E2

A laminated sheet was prepared having a non-heat-shrinkable fiber layer (basis weight: 15 g/m$^2$) and a heat-shrinkable fiber layer (basis weight: 15 g/m$^2$) for the upper layer and lower layer, respectively. The non-heat-shrinkable fiber layer was a web having a content of PET/PE core-sheath composite fibers (3.3 dtex×51 mm, 4% titanium oxide content in core) of 100 mass %, and the heat-shrinkable fiber layer (latent crimping fiber layer) was a web having a content of coPP (PP copolymer/PP side-by-side composite fibers (2.2 dtex×51 mm) of 20 mass % and a content of PET/PE core-sheath composite fibers (2.2 dtex×44 mm, 4% titanium oxide content in core) of 80 mass %. Both fibers were subjected to hydrophilicizing treatment with a surfactant.

This was followed by embossing treatment and heat treatment in the same manner as Test Example 8. The basis weight before heat treatment was 35 g/m$^2$, and the basis weight after heat treatment was 170 g/m$^2$. Thus, a top sheet having an irregular structure formed on the skin contact surface was prepared (the absorbent body comprising pulp at a basis weight of 250 g/m$^2$, the interface between the top sheet and the absorbent body being joined with a hot-melt adhesive at a basis weight of a 5 g/m$^2$), and the top sheet was used to produce a sanitary napkin, coating a blood slipping agent (triglyceride) on the skin contact surface of the top sheet at a basis weight of 3 g/m$^2$. A blood slipping agent-coated article was used as sample E1, and a non-blood slipping agent-coated article was used as sample E2.

(2) Preparation of Samples F1 and F2

Samples F1 and F2 were fabricated in the same manner as samples E1 and E2, except that the mass mixing ratio in the heat-shrinkable fiber layer (latent crimping fiber layer) was changed to coPP (PP copolymer)/PP side-by-side composite fibers: PET/PE core-sheath composite fibers=5:5. The basis weight before heat treatment was 17.5 g/m$^2$, and the basis weight after heat treatment was 165 g/m$^2$.

(3) Measurement of Blood Residue Rate

[Test Methods]
An acrylic board with an opened hole (200 mm×100 mm, 125 g, with a 40 mm×10 mm hole opened at the center) was placed on the skin contact surface of each sample, and 3 mL of horse EDTA blood at 37±1° C. (obtained by adding ethylenediaminetetraacetic acid (EDTA) to horse blood to prevent coagulation) was dropped through the hole using a pipette (first time), and after 1 minute, 3 mL of horse EDTA blood at 37±1° C. was again added dropwise through the acrylic board hole with a pipette (second time). The dropping rate was 90 mL/min. After the second blood dropping, it was allowed to stand for 1 minute and the blood residue rate was calculated by the following formula.

Blood residue rate (%)=100×(sample mass after test−initial sample mass)/6

[Results]
The blood residue rate was 17.3% for sample E1, 26.6% for sample E2, 10.2% for sample F1 and 17.8% for sample F2.

This test example demonstrated that even when using a top sheet having an irregular structure formed on the skin contact surface by heat shrinkage of the heat-shrinkable fibers, it is possible for the blood slipping agent to exhibit a blood-slipping function and to allow menstrual blood to rapidly migrate from the top sheet into the absorbent body.

It was also shown that a greater amount of latent crimping fibers increases the amount of blood residue. This is presumably because when crimping of the latent crimping fibers becomes developed by heat treatment, the fibers form coils, thereby increasing the blood retentivity. On the other hand, the blood slipping agent exhibits a blood slipping function, allowing menstrual blood to rapidly migrate from the top sheet into the absorbent body before the blood becomes held inside the coiled fibers.

Test Example 10

(1) Preparation of Samples G1 and G2

PET/PE core-sheath composite fibers (3.3 dtex×51 mm, 4% titanium oxide content in core) were used to form a heat-extendable fiber layer. The heat-extendable fiber layer was a web with a basis weight of 44 g/m$^2$ and a thickness of 1.6 mm. The web was subjected to embossing at a treatment temperature of 130° C., a pressing time of 1 second and a pressure of 15 kgf/mm$^2$. For this there was used an emboss pattern having rhomboid-shaped projections with 9 mm sides and 15 mm long diagonals, arranged at spacings of 1 mm. Projections with widths of 1 mm were formed on the web surface by sections with spacings of 1 mm.

This was followed by air-through treatment with a hot air drier (line speed: 5 m/min, wind speed: 1.5 m/sec, temperature: 135° C.), to form the web into a nonwoven fabric. Thus, a top sheet having an irregular structure formed on the skin contact surface was prepared, and the top sheet was used to produce a sanitary napkin (the absorbent body comprising pulp at a basis weight of 250 g/m$^2$, and the interface between the top sheet and the absorbent body being joined with a hot-melt adhesive at a basis weight of a 5 g/m$^2$), coating a blood slipping agent (triglyceride) on the skin contact surface of the top sheet at a basis weight of 3 g/m$^2$. A blood slipping agent-coated article was used as sample G1, and a non-blood slipping agent-coated article was used as sample G2.

(2) Preparation of Samples H1 and H2

PET/PE core-sheath composite fibers (3.3 dtex×51 mm, 4% titanium oxide content in core) were used to form a non-heat-extendable fiber layer. The heat-extendable fiber layer was a web with a basis weight of 44 g/m$^2$ and a thickness of 1.2 mm. The web was used to prepare samples H1 and H2 in the same manner as samples G1 and G2.

(3) Measurement of Penetration Time, Absorbent Body-Migration Time (Drain Time) and Rewetting Rate The penetration time, absorbent body-migration time (drain time) and rewetting rate were measured in the same manner as Test Example 8.

With sample G1, the liquid permeation rate (1st time) was 2 seconds, the liquid permeation rate (2nd time) was 2.59 seconds, the absorbent body migration rate (1st time) was 5.29 seconds, the absorbent body migration rate (2nd time) was 15.89 seconds, and the rewetting rate was 8.9%.

With sample G2, the liquid permeation rate (1st time) was 2 seconds, the liquid permeation rate (2nd time) was 2.84 seconds, the absorbent body migration rate (1st time) was longer than 60 seconds, the absorbent body migration rate (2nd time) was longer than 60 seconds, and the rewetting rate was 17.2%.

With sample H1, the liquid permeation rate (1st time) was 2 seconds, the liquid permeation rate (2nd time) was 2.75 seconds, the absorbent body migration rate (1st time) was 12.11 seconds, the absorbent body migration rate (2nd time) was 40 seconds, and the rewetting rate was 11.7%.

With sample H2, the liquid permeation rate (1st time) was 2 seconds, the liquid permeation rate (2nd time) was 3.19 seconds, the absorbent body migration rate (1st time) was longer than 60 seconds, the absorbent body migration rate (2nd time) was longer than 60 seconds, and the rewetting rate was 20%.

This test example demonstrated that even when using a top sheet having an irregular structure formed on the skin contact surface by heat stretching of the heat-extendable fibers, it is possible for the blood slipping agent to exhibit a blood-slipping function and to allow menstrual blood to rapidly migrate from the top sheet into the absorbent body.

Also, it is presumed that because heat stretching of the heat-extendable fibers increases the bulk and lowers the density, the system using heat-extendable fibers provided more satisfactory results than the system using non-heat-extendable fibers. Presumably this is because the closed regions surrounded by embossed sections readily extend in the thickness direction during extension of heat-extendable fibers.

REFERENCE SIGNS LIST

1 Sanitary napkin (absorbent article)
2 Top sheet (liquid-permeable layer)
3 Back sheet (liquid-impermeable layer)
4 Absorbent body
5 Compressed section
8 Projection
9 Recess

The invention claimed is:

1. An absorbent article comprising a liquid-permeable layer, a liquid-impermeable layer and an absorbent body situated between the liquid-permeable layer and the liquid-impermeable layer,
wherein the liquid-permeable layer has a first layer with a skin contact surface and a non-skin contact surface,
the first layer is a layer formed by heat stretching of a heat-extendable fiber layer that has been partially compressed by compressed sections,
a projection bulges out on the skin contact surface by heat stretching of the heat-extendable fiber layer at least in the excretory opening contact region of the skin contact surface, and
at least the projection of the excretory opening contact region are coated with a blood slipping agent having a 40° C. kinematic viscosity of 0.01 to 80 mm$^2$/s, a water holding percentage of 0.01 to 4.0 mass % and a weight-average molecular weight of less than 1,000.

2. The absorbent article according to claim 1, wherein the liquid-permeable layer has a second layer on the non-skin contact surface side of the first layer.

3. The absorbent article according to claim 2, wherein the density of the second layer is greater than the density of the first layer.

4. The absorbent article according to claim 3, wherein the density of the second layer is 0.1 g/cm$^3$ or less.

5. The absorbent article according to claim 3, wherein the density of the first layer is 0.05 g/cm$^3$ or less.

6. The absorbent article according to claim 1, wherein the Inorganic Organic Balance (IOB) of the blood slipping agent is 0.00 to 0.60.

7. The absorbent article according to claim 1, wherein the blood slipping agent is selected from the group consisting of the following items (i)-(iii), and any combination thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety;
with the proviso that when 2 or more oxy groups are inserted in the compound of (ii) or (iii), the oxy groups are not adjacent.

8. The absorbent article according to claim 1, wherein the blood slipping agent is selected from the group consisting of the following items (i')-(iii'), and any combination thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;
with the proviso that when 2 or more same or different bonds are inserted in the compound of (ii') or (iii'), the bonds are not adjacent.

9. The absorbent article according to claim 1, wherein the blood slipping agent is selected from the group consisting of the following items (A)-(F), and any combination thereof:
(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

10. The absorbent article according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, and any combination thereof.

11. The absorbent article according to claim 1, wherein the blood slipping agent has a vapor pressure of 0.00 to 0.01 Pa at 1 atmosphere, 40° C.

\* \* \* \* \*